(12) United States Patent
Smith

(10) Patent No.: US 12,390,584 B2
(45) Date of Patent: Aug. 19, 2025

(54) AMBULATORY INFUSION PUMPS AND ASSEMBLIES FOR USE WITH SAME

(71) Applicant: MEDTRONIC MINIMED, INC., Northridge, CA (US)

(72) Inventor: Roger E. Smith, Ivins, UT (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 448 days.

(21) Appl. No.: 17/580,090

(22) Filed: Jan. 20, 2022

(65) Prior Publication Data

US 2022/0133993 A1   May 5, 2022

Related U.S. Application Data

(63) Continuation of application No. 16/038,049, filed on Jul. 17, 2018, now Pat. No. 11,260,171.
(Continued)

(51) Int. Cl.
*A61M 5/14* (2006.01)
*A61M 5/142* (2006.01)
(Continued)

(52) U.S. Cl.
CPC ........ *A61M 5/158* (2013.01); *A61M 5/14244* (2013.01); *A61M 5/14248* (2013.01);
(Continued)

(58) Field of Classification Search
CPC .......... A61M 5/158; A61M 2005/1585; A61M 5/14248; A61M 2005/14252; A61M 2005/1581; A61M 2005/1587
See application file for complete search history.

(56) References Cited

U.S. PATENT DOCUMENTS

| | | |
|---|---|---|
| 1,771,219 A | 7/1930 | Hein |
| 3,662,753 A | 5/1972 | Tassell |
| | (Continued) | |

FOREIGN PATENT DOCUMENTS

| | | |
|---|---|---|
| CA | 2406026 | 10/2002 |
| CA | 2741716 | 9/2003 |
| | (Continued) | |

OTHER PUBLICATIONS

Australian Application 2019284140 Examination Report No. 2; dated Oct. 7, 2020; 4 pages; (MD50015AUD3).
(Continued)

*Primary Examiner* — Courtney B Fredrickson
(74) *Attorney, Agent, or Firm* — Fortem IP LLP

(57) ABSTRACT

According to an aspect, a cannula insertion mechanism includes a seal and a cannula carrier. The seal is configured to surround an opening of a housing, the seal including a first seal surface and a second seal surface, the first seal surface facing toward the opening, and the second seal surface facing away from the opening. The cannula carrier is configured to drive a cannula in a first direction through the opening of the housing, the cannula carrier having a first carrier surface and a second carrier surface, the first carrier surface being configured to exert a compression force on the second seal surface when the cannula carrier drives the cannula in the first direction, thereby causing the first seal surface to expand in a second direction to engage the second carrier surface via a clamping force.

20 Claims, 25 Drawing Sheets

Related U.S. Application Data

(60) Provisional application No. 62/528,486, filed on Jul. 4, 2017.

(51) Int. Cl.
   *A61M 5/145* (2006.01)
   *A61M 5/158* (2006.01)
   *A61B 17/34* (2006.01)

(52) U.S. Cl.
   CPC ....... *A61M 5/1452* (2013.01); *A61B 17/3415* (2013.01); *A61M 2005/14252* (2013.01); *A61M 2005/14268* (2013.01); *A61M 2005/14506* (2013.01); *A61M 2005/1583* (2013.01); *A61M 2005/1585* (2013.01); *A61M 2205/18* (2013.01); *A61M 2205/3317* (2013.01); *A61M 2205/8206* (2013.01)

(56) References Cited

U.S. PATENT DOCUMENTS

| | | |
|---|---|---|
| 4,379,453 A | 4/1983 | Baron |
| 4,886,499 A | 12/1989 | Cirelli et al. |
| 5,176,662 A * | 1/1993 | Bartholomew ... A61M 25/0606 604/513 |
| 5,257,980 A | 11/1993 | Van Antwerp et al. |
| 5,355,067 A | 10/1994 | Tabuchi |
| 5,364,510 A | 11/1994 | Carpio |
| 5,527,299 A * | 6/1996 | Cude ................. A61M 39/1055 604/905 |
| 5,549,583 A * | 8/1996 | Sanford ................. A61M 39/10 604/905 |
| 5,584,813 A | 12/1996 | Livingston et al. |
| 5,779,665 A | 7/1998 | Mastrototaro et al. |
| 5,785,850 A * | 7/1998 | Lynch ................... B01D 29/15 210/DIG. 17 |
| 5,851,197 A | 12/1998 | Marano et al. |
| 5,951,521 A | 9/1999 | Mastrototaro et al. |
| 6,056,718 A | 5/2000 | Funderburk et al. |
| 6,093,172 A | 7/2000 | Funderburk et al. |
| 6,254,586 B1 | 7/2001 | Mann et al. |
| 6,293,925 B1 | 9/2001 | Safabash et al. |
| 6,461,331 B1 | 10/2002 | Van Antwerp et al. |
| 6,520,938 B1 | 2/2003 | Funderburk et al. |
| 6,607,509 B2 | 8/2003 | Bobroff et al. |
| 6,749,587 B2 | 6/2004 | Flaherty |
| 6,902,207 B2 | 6/2005 | Lickliter |
| 6,997,907 B2 | 2/2006 | Safabash et al. |
| 7,207,974 B2 | 4/2007 | Safabash et al. |
| 7,303,543 B1 | 12/2007 | Maule et al. |
| 7,318,816 B2 | 1/2008 | Bobroff et al. |
| 7,329,239 B2 | 2/2008 | Safabash et al. |
| 7,455,663 B2 | 11/2008 | Bikovsky |
| 8,282,366 B2 | 10/2012 | Hilber et al. |
| 8,430,849 B2 | 4/2013 | Smith et al. |
| 8,448,523 B2 | 5/2013 | Richter |
| 8,568,361 B2 | 10/2013 | Yodfat et al. |
| 8,777,901 B2 | 7/2014 | Smith et al. |
| 8,905,972 B2 | 12/2014 | Smith et al. |
| 8,915,879 B2 | 12/2014 | Smith et al. |
| 9,114,208 B2 | 8/2015 | Smith et al. |
| 9,216,249 B2 | 12/2015 | Smith et al. |
| 9,308,320 B2 | 4/2016 | Smith et al. |
| 9,381,300 B2 | 7/2016 | Smith et al. |
| 9,498,573 B2 | 11/2016 | Smith et al. |
| 9,750,875 B2 | 9/2017 | Smith et al. |
| 9,839,747 B2 | 12/2017 | Smith et al. |
| 10,272,196 B2 | 4/2019 | Smith et al. |
| 10,342,918 B2 | 7/2019 | Politis et al. |
| 10,398,853 B2 | 9/2019 | Huwiler et al. |
| 2003/0161744 A1 | 8/2003 | Vilks et al. |
| 2004/0158207 A1 | 8/2004 | Hunn et al. |
| 2005/0020980 A1 | 1/2005 | Inoue et al. |
| 2005/0209804 A1 | 9/2005 | Basso et al. |
| 2006/0095014 A1 | 5/2006 | Ethelfeld |
| 2007/0191772 A1 | 8/2007 | Wojcik |
| 2008/0051738 A1 * | 2/2008 | Griffin ................. A61M 5/158 604/272 |
| 2008/0269687 A1 | 10/2008 | Chong et al. |
| 2008/0319416 A1 | 12/2008 | Yodfat et al. |
| 2009/0099521 A1 | 4/2009 | Gravesen et al. |
| 2009/0166978 A1 | 7/2009 | Hoffmann et al. |
| 2009/0198215 A1 | 8/2009 | Chong et al. |
| 2010/0100056 A1 | 4/2010 | Cawthon et al. |
| 2010/0217105 A1 | 8/2010 | Yodfat et al. |
| 2011/0034883 A1 | 2/2011 | Gyrn et al. |
| 2011/0144586 A1 | 6/2011 | Michaud et al. |
| 2011/0196337 A1 | 8/2011 | Brandt et al. |
| 2011/0224603 A1 | 9/2011 | Richter |
| 2011/0238015 A1 | 9/2011 | Matusch |
| 2012/0078170 A1 | 3/2012 | Smith et al. |
| 2012/0078181 A1 | 3/2012 | Smith et al. |
| 2012/0078182 A1 | 3/2012 | Smith et al. |
| 2012/0078183 A1 | 3/2012 | Smith et al. |
| 2012/0078184 A1 | 3/2012 | Smith et al. |
| 2012/0078185 A1 | 3/2012 | Smith et al. |
| 2012/0078217 A1 | 3/2012 | Smith et al. |
| 2012/0078222 A1 | 3/2012 | Smith et al. |
| 2012/0184907 A1 | 7/2012 | Smith et al. |
| 2012/0184909 A1 | 7/2012 | Gyrn |
| 2012/0215163 A1 | 8/2012 | Hanson et al. |
| 2012/0245515 A1 | 9/2012 | Calasso et al. |
| 2013/0138078 A1 | 5/2013 | Smith et al. |
| 2013/0237781 A1 | 9/2013 | Gyrn |
| 2013/0310801 A1 | 11/2013 | Yodfat et al. |
| 2014/0058353 A1 | 2/2014 | Politis et al. |
| 2014/0228802 A1 | 8/2014 | Mackey et al. |
| 2014/0296786 A1 | 10/2014 | Servansky et al. |
| 2015/0073386 A1 | 3/2015 | Smith et al. |
| 2015/0133855 A1 | 5/2015 | Smith et al. |
| 2016/0058474 A1 | 3/2016 | Peterson et al. |
| 2016/0089491 A1 | 3/2016 | Smith |
| 2017/0232191 A1 | 8/2017 | Smith et al. |
| 2018/0185572 A1 | 7/2018 | Smith et al. |
| 2018/0318502 A1 | 11/2018 | Smith et al. |
| 2019/0015585 A1 | 1/2019 | Smith |
| 2019/0076599 A1 | 3/2019 | Smith |
| 2019/0321543 A1 | 10/2019 | Smith et al. |
| 2020/0360600 A1 | 11/2020 | Smith et al. |

FOREIGN PATENT DOCUMENTS

| | | |
|---|---|---|
| CA | 2632995 A1 | 7/2007 |
| CA | 2659616 | 2/2008 |
| CA | 2921304 | 2/2011 |
| CA | 2842951 | 7/2011 |
| CN | 101574550 A | 11/2009 |
| CN | 101745163 A | 6/2010 |
| JP | 59127595 A | 7/1984 |
| JP | 2002078386 A | 3/2002 |
| JP | 2008168297 A | 7/2008 |
| JP | 2009030311 A | 2/2009 |
| JP | 2015521948 A | 8/2015 |
| WO | 198503007 A1 | 7/1985 |
| WO | 9858693 A1 | 12/1998 |
| WO | 2004091692 A2 | 10/2004 |
| WO | 2007094833 A1 | 8/2007 |
| WO | 2007140631 A1 | 12/2007 |
| WO | 2008063429 A2 | 5/2008 |
| WO | 2008082126 A | 7/2008 |
| WO | 2009101130 A1 | 8/2009 |
| WO | 2009125398 A2 | 10/2009 |
| WO | 2009158651 A2 | 12/2009 |
| WO | 2010051369 A1 | 5/2010 |
| WO | 2011146166 A1 | 11/2011 |
| WO | 2012040528 A1 | 3/2012 |
| WO | 2014011879 A2 | 1/2014 |
| WO | 2014116274 A | 7/2014 |
| WO | 2016133789 A2 | 8/2016 |

(56) References Cited

FOREIGN PATENT DOCUMENTS

WO    2017135936 A1    8/2017
WO    2017139723 A1    8/2017

OTHER PUBLICATIONS

CN Application No. 201680083837.4; English Translation of Office Action dated Aug. 6, 2020, 11 pages (MD50013CN).
CN Application No. 201780023000.5 First Office Action dated Feb. 3, 2021, Translation, 8 pages.
EP Office Action; Application No. 17706380.7-1122; Aug. 18, 2020; 7 pages; (MD50018EP).
Extended European Search Report; Application No. 20166121.2; Jul. 10, 2020; 12 pages.
Extended European Search Report; Application No. 19210609.4; Jun. 23, 2020; 5 pages. (MD50019EPD).
Jahn et al.; "Comparative Dose Accuracy of Durable and Patch Insulin Infusion Pumps"; Journal of Diabetes Science and Technology; 7(4); pp. 1011-1020; Jul. 2013.
JP Patent Application No. 2018-542219 Notice of Reasons for Refusal (translated) issued Dec. 1, 2020, 6 pages (MD50018JP).

* cited by examiner

AMBULATORY INFUSION PUMPS AND ASSEMBLIES FOR USE WITH SAME

CROSS-REFERENCE TO RELATED APPLICATIONS

This application is a continuation of U.S. application Ser. No. 16/038,049, filed Jul. 17, 2018, which claims the benefit of and priority to previously filed U.S. Provisional Patent Application Ser. No. 62/528,486, filed Jul. 4, 2017, which is incorporated herein by reference in its entirety.

FIELD

The present devices and methods relate generally to ambulatory infusion pumps and inserters and seals for those pumps.

BACKGROUND

Ambulatory infusion pumps (also referred to herein simply as "infusion pumps") are relatively small, at least substantially self-contained devices that are used to introduce drugs and other infusible substances (collectively "medicament") into patients' bodies. Some infusion pumps are configured to be worn on a belt, carried in a clothing pocket, or the like. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin. Other exemplary medicaments that may be introduced by an infusion pump include, but are not limited to, drugs that treat cancers and drugs that suppress the perception of pain.

Many conventional infusion pumps have improved patient health and quality of life. Nevertheless, the present inventors have determined that conventional infusion pumps are susceptible to a wide range of improvements. By way of example, but not limitation, the present inventors have determined that it would be desirable to provide an infusion pump that is smaller, simpler, more reliable, and less costly than conventional infusion pumps, while also being more accurate and user-friendly than conventional infusion pumps.

SUMMARY

The techniques of this disclosure generally relate to cannula insertion mechanisms. In one aspect, the present disclosure provides a cannula insertion mechanism including a seal and a cannula carrier. The seal is configured to surround an opening of a housing, the seal including a first seal surface and a second seal surface, the first seal surface facing toward the opening, and the second seal surface facing away from the opening. The cannula carrier is configured to drive a cannula in a first direction through the opening of the housing, the cannula carrier having a first carrier surface and a second carrier surface, the first carrier surface being configured to exert a compression force on the second seal surface when the cannula carrier drives the cannula in the first direction, thereby causing the first seal surface to expand in a second direction to engage the second carrier surface via a clamping force.

In another aspect, the disclosure provides a fluid delivery device that includes a housing and a cannula insertion mechanism. The cannula insertion mechanism includes a seal and a cannula carrier. The seal is configured to surround an opening of the housing, the seal including a first seal surface and a second seal surface, the first seal surface facing toward the opening, and the second seal surface facing away from the opening. The cannula carrier is configured to drive a cannula in a first direction through the opening of the housing, the cannula carrier having a first carrier surface and a second carrier surface, the first carrier surface being configured to exert a compression force on the second seal surface when the cannula carrier drives the cannula in the first direction, thereby causing the first seal surface to expand in a second direction to engage the second carrier surface via a clamping force.

BRIEF DESCRIPTION OF THE DRAWINGS

Detailed description of exemplary embodiments will be made with reference to the accompanying drawings.

DETAILED DESCRIPTION

Figure 1A:
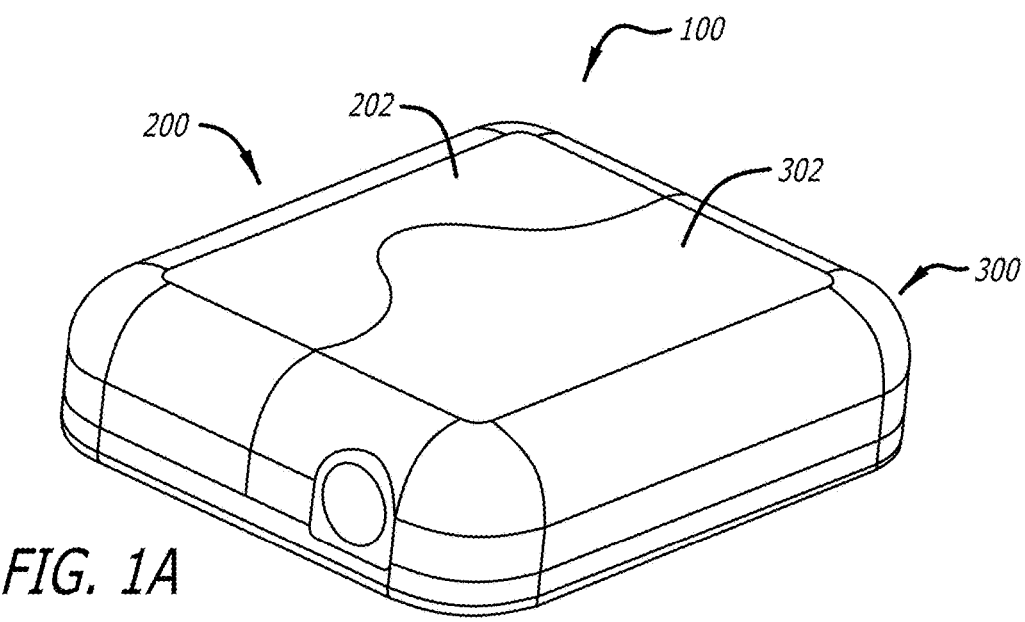
FIG. 1A is a perspective view of an exemplary infusion pump system in an assembled state.

The following is a detailed description of the best presently known modes of carrying out the inventions. This description is not to be taken in a limiting sense, but is made merely for the purpose of illustrating the general principles of the inventions.

It should also be noted here that the specification describes structures and methods that are especially well-suited for the subcutaneous delivery of high concentration insulin (i.e., U-200 insulin and above) such as U-500 insulin as well as lower concentration insulin such as U-100 insulin. Nevertheless, it should be appreciated that the present inventions are applicable to a wide variety of infusion pumps and medicaments. By way of example, but not limitation, the inventions may employ, for fluid displacement, a reservoir with a plunger, a fluid displacement device in the form of a plunger pusher, and a drive mechanism that includes a motor, or other fluid displacement devices, regardless of the type of reservoir employed, piston pumps (e.g., electromagnet pumps), MEMS pumps, peristaltic pumps and any other suitable pumps as well as corresponding drive mechanisms. Exemplary infusion pumps that include a reservoir with a plunger, sometimes in combination with a fluid displacement device in the form of a plunger pusher, and a drive mechanism, are described in U.S. patent application Ser. No. 12/890,207, filed Sep. 24, 2010, and corresponding U.S. Pat. No. 8,777,901, both of which are incorporated by reference in their entireties; in U.S. provisional patent application Ser. No. 62/057,273, filed Sep. 30, 2014, corresponding U.S. patent application Ser. No. 14/869,906, filed Sep. 29, 2015, and corresponding U.S. patent publication number 2016/0089491, each of which are incorporated by reference in their entireties; in U.S. provisional patent application Ser. No. 62/117,565, filed Feb. 18, 2015, corresponding U.S. patent application Ser. No. 15/042,093, filed Feb. 11, 2016, and corresponding U.S. patent publication number 2016/0235913, each of which are also incorporated by reference in their entireties; and in U.S. provisional patent application Ser. No. 62/294,941, filed Feb. 12, 2016, and corresponding U.S. patent application Ser. No. 15/430,513, filed Feb. 12, 2017, both of which are also incorporated by reference in their entireties. The present inventions are also applicable to medicaments such as, for example, drugs to mask pain, chemotherapy and other cancer related drugs, antibiotics, hormones, GLP-1, glucagon, various other drugs that include large molecules and proteins that may require a high level of delivery accuracy, as well as to relatively high concentration insulin (i.e., U-200 insulin and above) such as U-500 insulin, as well as lower concentration insulin, such as U-100 insulin. U.S. application Ser. No. 13/475,843, filed May 18, 2012, and corresponding U.S. Pat. No. 9,114,208, as well as aforementioned U.S. Pat. No. 8,777,901, aforementioned U.S. patent publication number 2016/0089491, and aforementioned U.S. patent application Ser. No. 15/430,513 each also describe patient interaction with and use of infusion pumps such as the exemplary infusion pumps described herein.

As noted above, some ambulatory infusion pumps are intended to be worn on a belt, carried in a pocket, or otherwise supported within a holder of some kind (referred to collectively as "pocket pumps"). Such infusion pumps transfer fluid from a reservoir to an infusion set by way of an elongate tube. Subcutaneous access may be obtained by way of a cannula in the infusion set. Other ambulatory infusion pumps are intended to be adhered to the skin above the delivery site (sometimes referred to as "patch pumps"). Here, the cannula or other subcutaneous access device may extend directly from the infusion device. In either case, these pumps infuse medicament through a cannula subcutaneously at a depth of approximately 6 mm. Given these modes of use, patients typically prefer the device to be as small as possible so it is more comfortable, less obtrusive, and less visible. In addition, patients want a device that is easy and convenient to use.

Figure 1B:
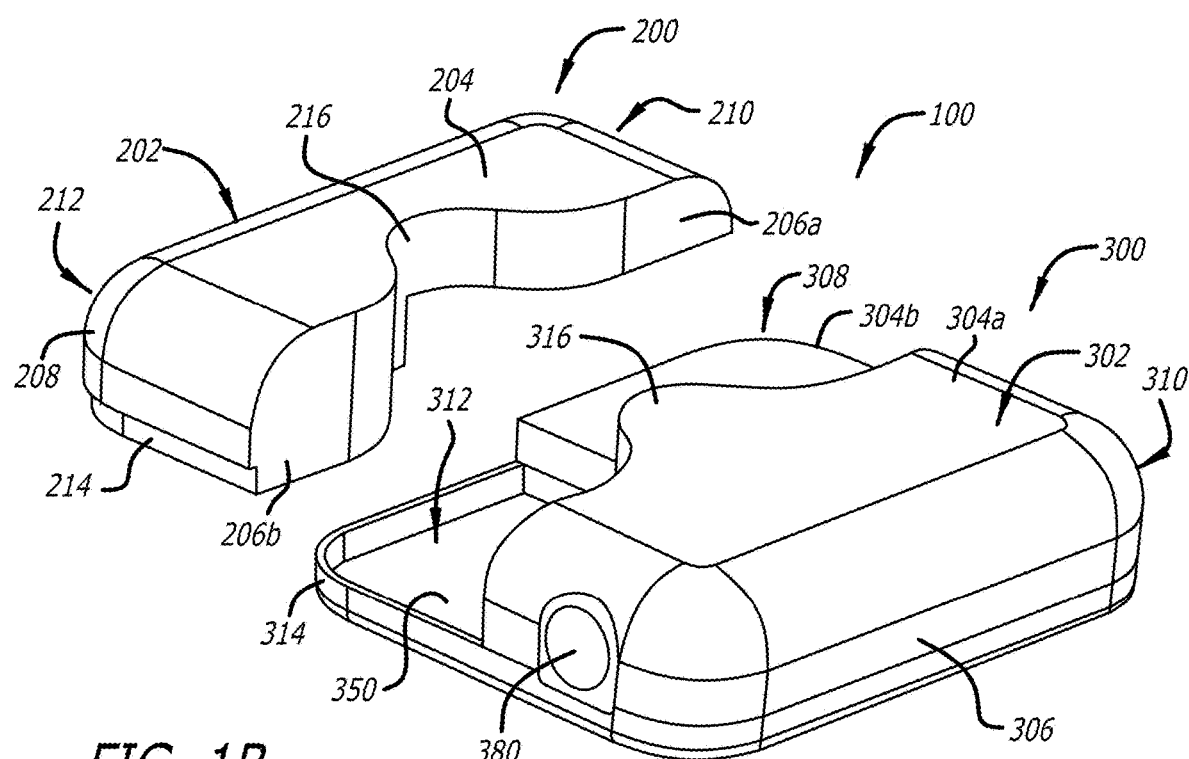
FIG. 1B is an exploded perspective view of the infusion pump system illustrated in FIG. 1A, including a durable assembly and a disposable assembly.
Figure 2:
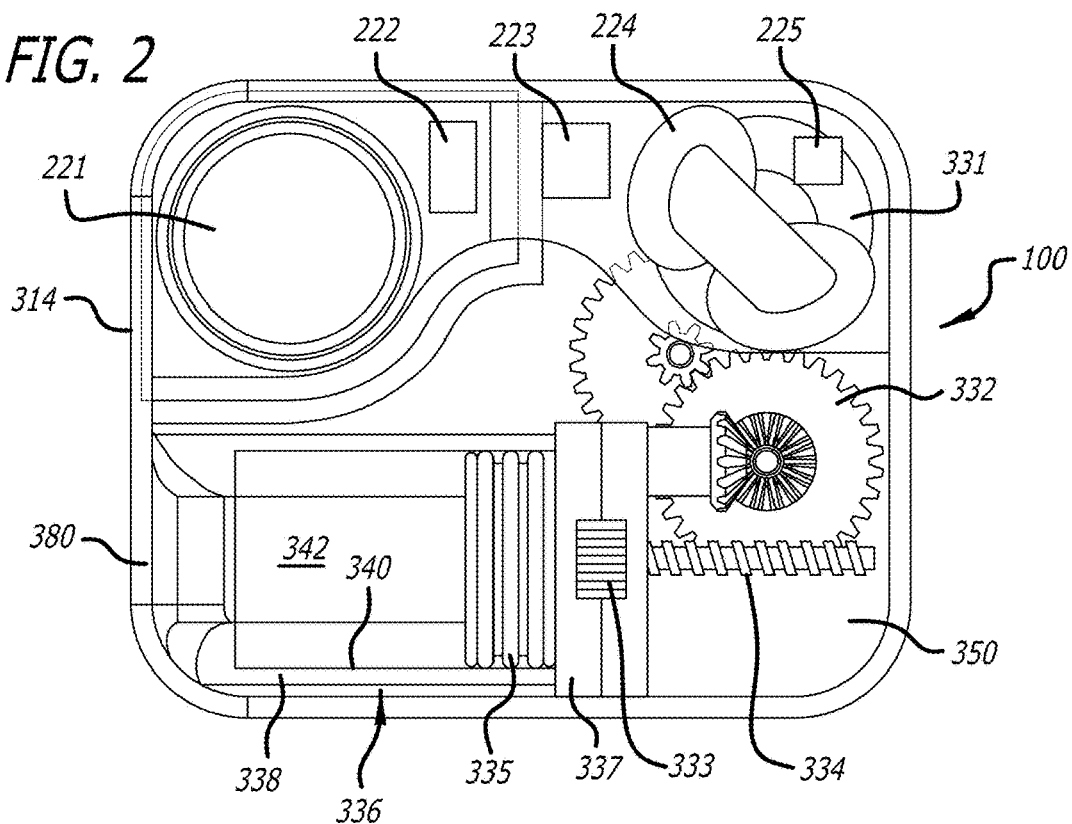
FIG. 2 is a top view of certain components of the infusion pump system illustrated in FIGS. 1A and 1B.

An exemplary ambulatory infusion system, which is generally represented by reference numeral 100 in FIGS. 1A, 1B, and 2, includes a durable assembly 200 and a disposable assembly 300. Exemplary durable assembly 200 includes a housing 202, one or more batteries or other energy supply 221, one or more capacitors or other energy storage 222, a microprocessor 223, a coil assembly 224 (which functions as a motor stator), and one or more Hall-effect sensors 225. Exemplary disposable assembly 300 includes a baseplate 350 supporting components such as a magnetic motor rotor 331, a gear train 332 including lead screw drive gear 333 in a reservoir support block 337, and a lead screw 334 attached to plunger 335, which is positioned in a medicament reservoir 336 that is mounted to the reservoir support block 337. The exemplary plunger 335 includes a core and a plurality of seals on the core. A cover 302, under which some or all of the magnetic motor rotor 331, gear train 332 (with drive gear 333), lead screw 334, plunger 335, and medicament reservoir 336 are located in various embodiments, may be mounted to the baseplate 350.

The lead screw drive gear 333, lead screw 334, plunger 335, medicament reservoir 336 and reservoir support block 337 may also be referred to collectively as a "reservoir assembly." Other exemplary reservoir assemblies, durable assemblies, disposable assemblies, and seal assemblies that may be employed in, for example, infusion system 100 are described below with reference to FIGS. 9A-9D, and in FIGS. 10A-10H.

The exemplary disposable assembly 300 may be secured to the exemplary durable assembly 200, as shown in FIGS. 1A and 2. To that end, the exemplary housing 202 includes a top wall 204, bottom walls 206a and 206b and a side wall 208 that together define a relatively thin housing portion 210 and a relatively thick housing portion 212. An indentation 214 is formed in the relatively thick portion 212. The exemplary cover 302 includes top walls 304a and 304b and a side wall 306 that together define a relatively thin cover portion 308 and a relatively thick cover portion 310. A portion of the baseplate 350 is not covered by the cover 302, thereby defining a recess 312 that is bordered by a wall 314 that extends around the baseplate (see also FIG. 4B). When the durable and disposable assemblies 200 and 300 are secured to one another in the manner illustrated in FIG. 1A, the relatively thick portion 212 of the housing 202 will reside in the recess 312 of the disposable assembly 300 (with the wall 314 in the indentation 214). The relatively thin portion 210 of the housing 202 will reside on the top wall 304b of the cover 302. The cover 302 also includes a projection 316 that mates with a recess 216 on the housing 202. Additionally, as is discussed in greater detail below, the disposable assembly 300 may be configured for different medicaments, such as different medicament concentrations, different medicament amounts, or different modes of system operation.

In other implementations, the cover 302 may be configured to cover fewer than all components on the baseplate 350. For example, a cover may be configured such that the magnetic motor rotor 331 and a portion of the gear train 332 are not under the cover, while the remaining components are under the cover. In still other implementations, the cover 302 may be omitted and the durable assembly 200 may be configured to cover all components on the baseplate 350. In yet other implementations, what is referred to in the present application as the "durable" assembly, may be disposable, resulting in a fully disposable system.

Figures 2A, 2B:
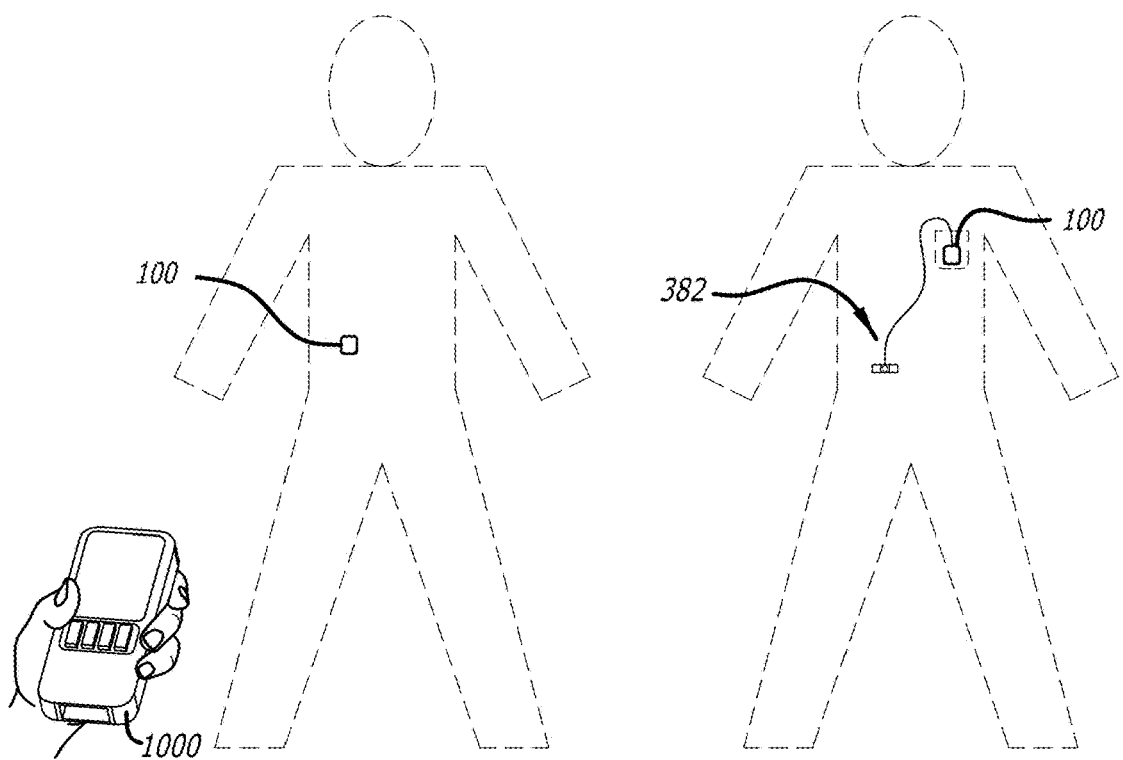
FIG. 2A is a schematic view showing a use of the infusion pump system illustrated in FIGS. 1A and 1B.
FIG. 2B is a schematic view showing another use of the infusion pump system illustrated in FIGS. 1A and 1B.

As discussed in U.S. Pat. No. 8,777,901 described above, and in U.S. application Ser. No. 13/300,574, filed Nov. 19, 2011, and corresponding U.S. Pat. No. 8,905,972, and in U.S. application Ser. No. 13/475,843, filed May 18, 2012, and corresponding U.S. Pat. No. 9,114,208, each of which are incorporated by reference in their entireties, ambulatory infusion systems that employ a reservoir on a baseplate may be configured for different types of use. For example, disposable assembly 300 may be adhered to the patient's skin and may be used in conjunction with a cannula (not shown) that is operatively connected to the reservoir 336 so that the system 100 may be deployed as a "patch-pump," as shown in FIG. 2A. Alternatively, as shown in FIG. 2B, the baseplate 350 of disposable assembly 300 may be configured to operably connect the reservoir 336 to an infusion set 382 (e.g., by way of the illustrated infusion set tube and a connector 380 shown in FIGS. 1B and 2) so that the system 100 may be deployed as a "pocket pump," a "belt-worn pump" or some other wearable pump. In other words, using the same durable assembly 200, the user may configure the system for use as "pocket pump" or a "patch pump" by simply selecting the appropriate disposable assembly and attaching the disposable assembly to the durable assembly. The user may also switch from one configuration to another, by simply removing one disposable assembly and replacing it with another disposable assembly. The connector 380 may also be used as a fill port, as discussed below.

It should therefore be noted that the present inventions include kits that contain various combinations of disposable assemblies, where at least two of the disposable assemblies may be different. Additionally or alternatively, kits or other packages may include various disposable assembly components, such as an infusion set and/or cannula inserter. Kits may also include a durable assembly. The disposable assemblies in such kits may also include the detection/identification instrumentalities discussed below. The components of the present kits (e.g., combination of various disposable assemblies and/or components) may be stored in a common package, with individual packages for each component if necessary, and provided to the user in the common package. Other components that may be provided in such kits include, but are not limited to, inserters that are preloaded with a cannula, and cleaning swabs. A recharger may also be provided in a kit that includes a durable assembly.

In addition to disposable assembly packaging and labeling, the different disposable assemblies may include visual cues to differentiate the various disposable assemblies. For instance, disposable assemblies with different concentrations of medicament or different medicament fill volumes may use different colors for the reservoir and/or baseplate of the disposable assembly, or mechanical features that ensure disposables are only able to attach to correctly programmed durables.

It should also be noted here that, but for the issue of priming, the dispensing procedures associated with an infusion system "patch pump" configuration, which may include a durable assembly 200 and a disposable assembly 300, are substantially the same as the dispensing procedures associated with a "pocket pump" configuration, which may also include an infusion set 382 (see FIG. 2B). With a "patch pump" configuration, priming is not necessary because the volume of the associated cannula will be very small and there is a direct connection between the cannula and the medicament reservoir. Priming is, however, required to fill the infusion set tube (FIG. 2B) in a "pocket pump" configuration before the onset of medicament delivery. For instance, 20-30 μl may be required to fill the entire infusion set tube and, accordingly, the priming procedure may involve the rapid delivery of 10-15 IUs of U-500 insulin to the tube. The present inventors have determined that it would be advantageous to prevent users from initiating a priming procedure when the system is in the "patch pump" configuration, with a cannula positioned to deliver medicament essentially directly from the medicament reservoir to the patient, because rapidly delivering 10-15 IUs of insulin to the patient could adversely affect patient health.

To prevent such undesirable outcomes, and for user convenience in other situations involving the choice between a variety of disposable assemblies (such as disposable assemblies with reservoirs containing different medicaments, different concentrations of a medicament, and/or varying amounts of medicaments), at least some of the present disposable assemblies may be provided with a baseplate identification device and at least some of the present disposable assemblies may be provided with structure that cooperate with a baseplate identification device in such a manner that the durable assembly microprocessor/controller can make a "baseplate type" determination. Exemplary baseplate identification instrumentalities and methodologies may be as described in aforementioned U.S. Pat. Nos. 8,777,901; 8,905,972; and 9,114,208. In addition, baseplate identification may be performed mechanically. For instance, a pin or rib may prevent attachment of certain disposable assemblies with certain durable assemblies. Additionally or alternatively, certain durable assemblies will simply not function with certain disposable assemblies.

Alternatively, the patient or a clinician may program the system, such as via a remote control, to indicate the type of disposable assembly attached. In a manner such as this, a patient can access a variety of medicaments for use with a single durable assembly.

Once the "baseplate type" determination is made (e.g., "patch pump" disposable assembly 300 versus a "pocket pump" with infusion set 382 attached), the durable assembly will proceed in a manner, or mode of operation, that is appropriate for the attached disposable assembly. For example, if "patch pump" disposable assembly 300 is detected, the durable assembly controller will not include priming as part of the delivery process and, in some implementations, will prevent the user from manually implementing a priming procedure. If, on the other hand, a "pocket pump" disposable assembly is detected, then the delivery process may include appropriate priming of the infusion set tube.

Whether configured as a "pocket pump" or a "patch pump," the system may be configured to provide basal delivery of medicament in accordance with a delivery profile provided by a physician by way of a clinician's programming unit. For example, the system may include a program that stores a number of delivery profiles (e.g., delivery profiles associated with a 24-hour delivery cycle, delivery profiles for particular situations such as sleep or illness, and the like). Each delivery profile specifies multiple doses (or pump "operations") over time, e.g., a particular number of doses at particular times or a particular number of doses per unit time. In some implementations, a dose may be the volume associated with the minimum controllable displacement of the plunger 335. The system may also be configured to provide bolus delivery in response to an instruction from a patient remote control 1000 (FIG. 2A). A bolus instruction may come in response to a high glucose level measurement in the case of a diabetic patient, an increase in pain level in the case of a pain management patient, or some other symptom. The system may also be configured to perform other functions, such as ending medicament delivery in response to instructions from patient remote control 1000.

The present infusion pumps may be used in conjunction with a wide variety of remote controls. Such remote controls may be used to, for example, allow the user to transmit instructions to the durable assembly 200 or facilitate communication between durable assembly 200 and the user (e.g., an alarm condition message or other message concerning the conditions of system 100). An exemplary remote control 1000 (FIG. 2A) may be configured to facilitate one, some, or all of the following operations: (1) turning the remote control 1000 on or off, (2) associating (or "assigning") the remote control 1000 to the durable assembly 200, (3) obtaining status information such as medicament level, battery charge level, and/or alarm conditions, (4) silencing the durable assembly's alarm, (5) selecting options that may be associated with the durable assembly's alarm such as type of alarm (audible, palpable, visible or combinations thereof) and strength/volume of alarm, (6) connecting remote control 1000 to a computer to, for example, update remote control or durable assembly firmware, load and delete delivery profiles stored in the durable assembly or remote control, and otherwise reprogram the durable assembly or remote control, (7) selecting medicament options such as medicament concentrations, (8) selecting and initiating a stored medicament delivery profile, (9) increasing and decreasing medicament dose rate, and/or (10) pausing a dispensing operation. A user may pause delivery in order to remove or replace a patient applied structure (e.g., a disposable assembly), adjust for a current or anticipated changed body condition (e.g., low glucose, vigorous exercise), follow a physician's suggestion, or disconnect the durable assembly from the body for any other reason.

The exemplary remote control 1000 (FIG. 2A) may be configured to generate an indicator, based on information from a microprocessor 223 for durable assembly 200, that is indicative of, for instance, the amount of time remaining in the current dispensing program, the amount of time until the next disposable assembly replacement, etc. The indicator may be audible, visible, palpable or combinations thereof. A time remaining indicator may be useful for a variety of reasons. For example, knowledge of the time remaining before the next disposable assembly replacement allows the patient to determine, based at least in part on the current time of day and upcoming events (e.g., travel or sleep), whether or not it would be more convenient to replace the disposable assembly at a time before the end of the dispensing program.

As described above, parts of the present systems may be considered the reusable parts, while other parts may be considered the disposable parts. In the illustrated embodiments, the durable assembly 200, which may include structures such as microprocessor 223 and coil assembly 224, is reusable, while exemplary disposable assemblies 300, which may include structures such as a motor rotor 331 and reservoir 336 on a baseplate 350, are disposable. In other embodiments, the present systems may be fully disposable.

With respect to dimensions, some embodiments of the exemplary infusion pump system 100 and the embodiments below may have the following dimensions: length dimensions of about 35-60 mm; width dimensions of about 30-45 mm; and overall thickness or height dimensions of about 8-18 mm. Suitable housing materials include, but are not limited to, plastic or other materials having a modulus of elasticity of 0.2-1.0 million psi.

Exemplary durable assembly microprocessors and associated circuitry; rechargeable batteries and associated battery rechargers and recharging methods; battery and recharging management; temperature sensors; and exemplary alarms and alarm conditions are described in more detail in aforementioned U.S. Pat. Nos. 8,777,901; 8,905,972; and 9,114,208.

Figure 3A:
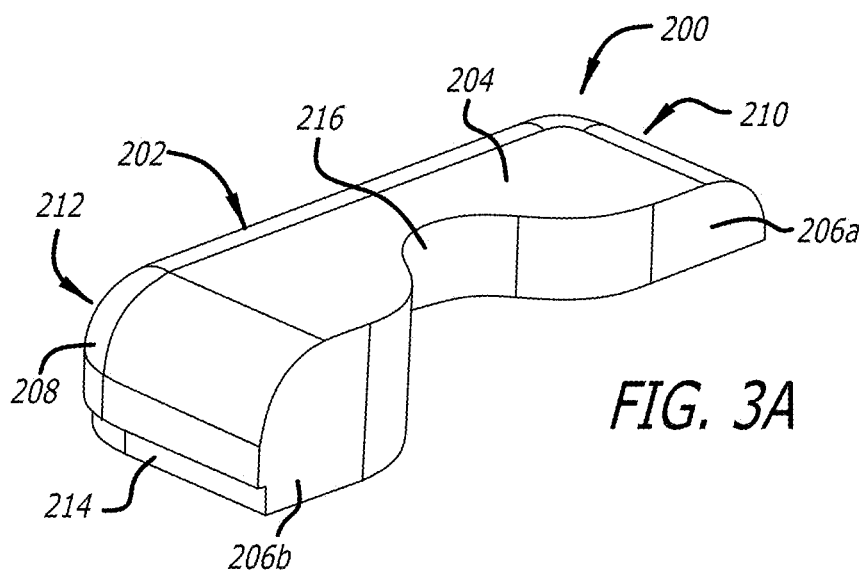
FIG. 3A is a perspective view of an exemplary durable assembly.
Figure 3B:
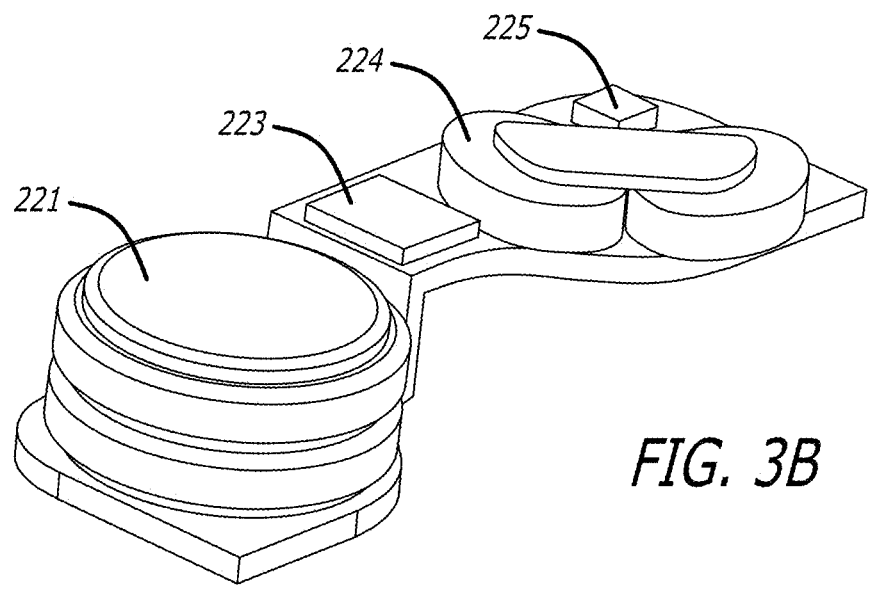
FIG. 3B is a perspective view of certain components of the durable assembly illustrated in FIG. 3A.

Turning now to FIGS. 3A and 3B, an exemplary durable assembly 200 may include a power source such as one or more batteries 221, temporary power storage such as one or more capacitors 222 (see FIGS. 2 and 5B), a controller such as microprocessor 223, a coil assembly 224, and a Hall-effect sensor 225. Those of skill in the art will appreciate that including the motor's coil assembly 224 and all other electronics within the durable assembly 200 reduces the cost and complexity of disposable assembly 300. In addition, the microprocessor 223 provides flexibility to include features such as user data storage, programs, programmability, adjustability, a display, buttons, wireless communication protocols, or the like to the pump 100. Durable assembly 200 may also be molded with locking features that snap onto the disposable assembly 300, but that also allow removal of the durable assembly 200 from the disposable assembly 300 either while the disposable assembly remains in place on the patient (after medicament delivery has been paused), or after the entire system has been removed from the patient.

The power source may be one or more commercially available batteries, such as a commercially available zinc-air battery or lithium polymer battery. The batteries may be selected to have sufficient capacity to operate the system for certain delivery amounts or delivery times, such as for over 400 units of delivered insulin. The optional power storage may be one or more commercially available capacitors or super-capacitors or other temporary storage device(s).

Figure 4A:
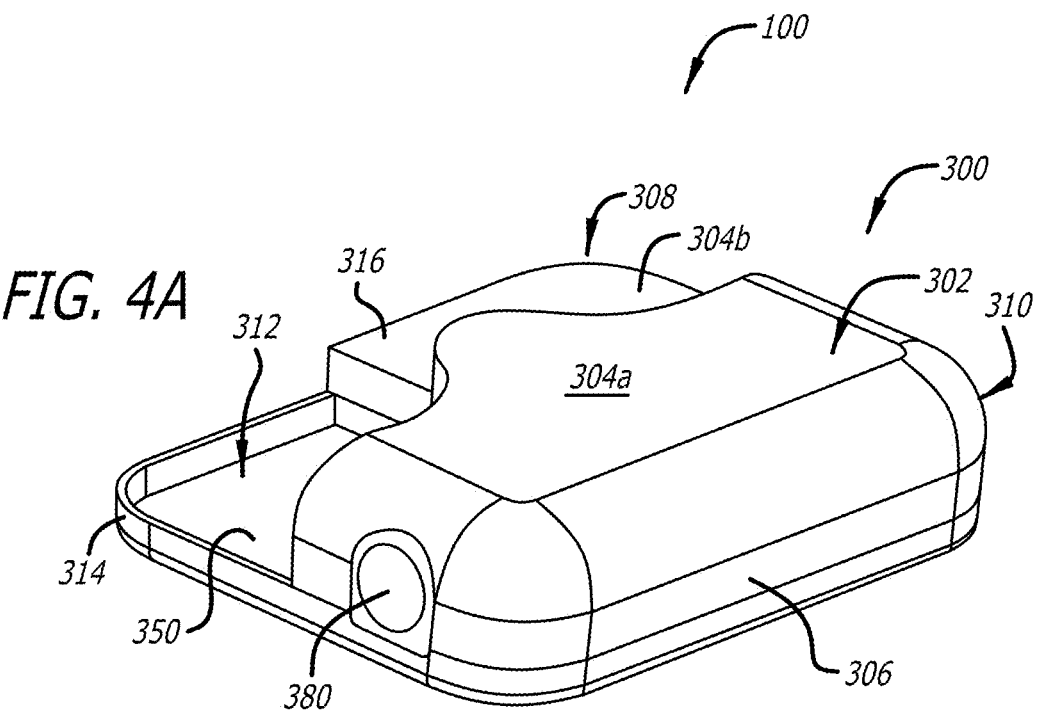
FIG. 4A is a perspective view of an exemplary disposable assembly.
Figure 4B:
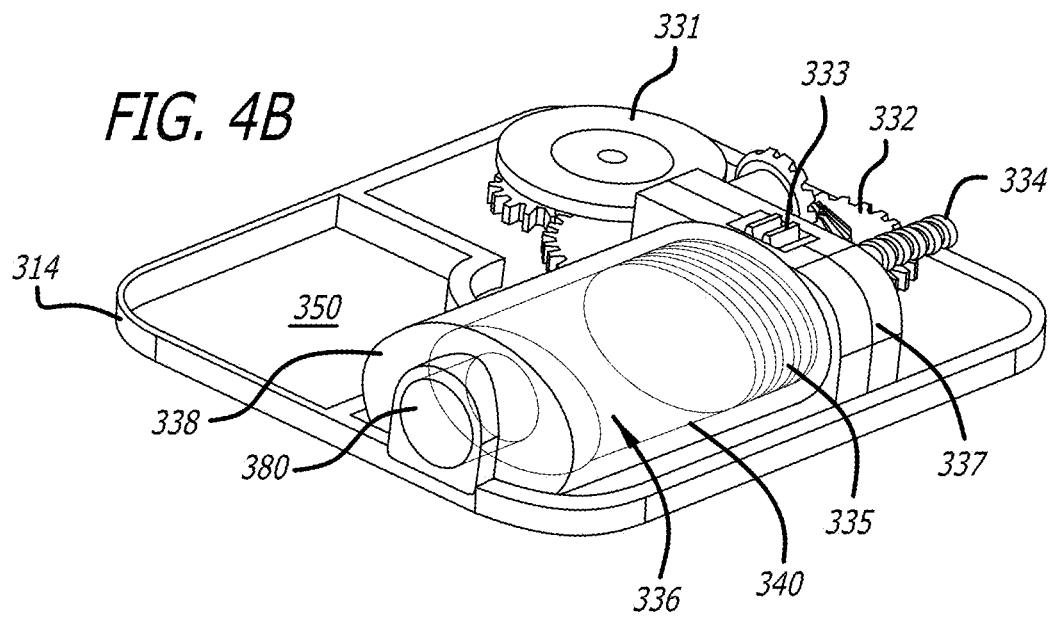
FIG. 4B is a perspective view of certain components of the disposable assembly illustrated in FIG. 4A.

Turning now to FIGS. 4A and 4B, an exemplary disposable assembly 300 may include baseplate 350 and components such as a reservoir 336, a plunger 335 within the reservoir and connected to lead screw 334, and a magnetic motor rotor 331 mechanically attached through gear train 332 to affect rotation of the lead screw drive gear 333, which causes translation of the lead screw 334 and plunger 335 within reservoir 336. The cover 302 is positioned over these components in the illustrated embodiment. The exemplary baseplate 350 includes an adhesive backing for attachment to the patient with a removable adhesive cover. The baseplate 350 may also be molded with baseplate locking features that snap onto the durable assembly 200 (such as magnets molded into the housings of each assembly), and that also allows removal of the durable assembly 200 from the disposable assembly 300.

Referring to FIGS. 2 and 4B, the exemplary reservoir 336 includes a barrel 338 with an inner surface 340 defining a fluid storage volume 342 and an oval cross-section, but other shapes (such as circular) are possible as is discussed below with reference to FIG. 9E. A plunger 335 with a matching cross-sectional shape fits within the barrel and carries a fluid seal such as, but not limited to, o-rings, to seal the medicament within the storage volume 342. Exemplary plunger 335 may be formed from, e.g., rubber and include three o-ring seals. The reservoir 336 includes the aforementioned connector 380 that may be used for filling reservoir 336, or for attaching a cannula for "patch-pump" type configurations, or for connecting (potentially via an appropriate adapter(s)) an infusion set for "pocket-pump" type configurations. The plunger 335 moves within the barrel 338 to vary the volume of medicament within the storage volume 342. Reservoir 336 may be, for instance, prefilled or user-filled with U-500 insulin in various volumes to suit the patient use profile. In other instances, lower concentrations of insulin, such as U-100 insulin and U-200 insulin, may be employed. A plug may be inserted in the connector 380 to maintain a sterile environment until use. The plug may be removed by the patient before use, or connector 380 may be configured for one use (sealed until penetrated), or other possibilities, including those described in more detail in aforementioned U.S. patent application Ser. No. 15/430,513.

Additional exemplary baseplates for use with the disposable assemblies of the present inventions, as well as exemplary cannula designs, fluidic connection between a medicament reservoir and the cannula, cooperation between the cannula and disposable assemblies (for instance, to prevent axial movement of the cannula relative to the baseplate and patient), attachment of an infusion set to the reservoir of the disposable assembly, configurations and uses of a non-delivery baseplate, arrangements and structures for attaching disposable and durable assemblies, skin adhesive designs, and various occlusion sensors, may be as described in U.S. patent application Ser. No. 12/890,207, filed Sep. 24, 2010 and corresponding U.S. Pat. No. 8,777,901, as well as aforementioned U.S. Pat. Nos. 8,905,972 and 9,114,208.

Figure 5A:
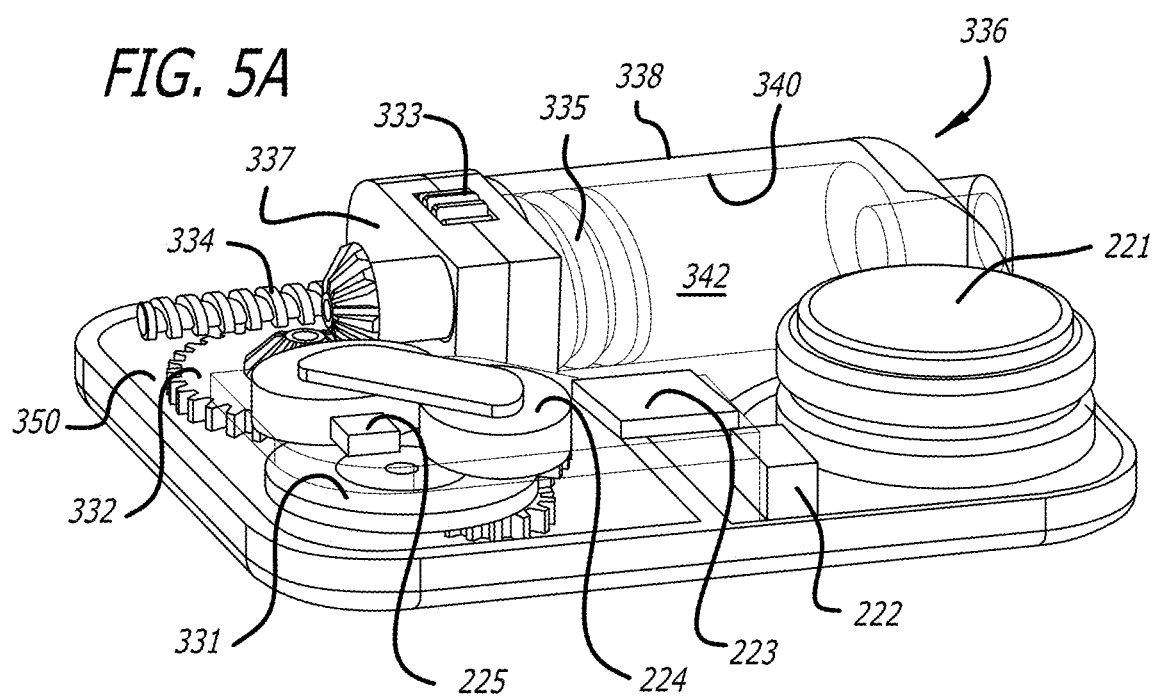
FIG. 5A is a perspective view of certain components of a durable assembly and a disposable assembly of an exemplary infusion pump system.
Figure 5B:
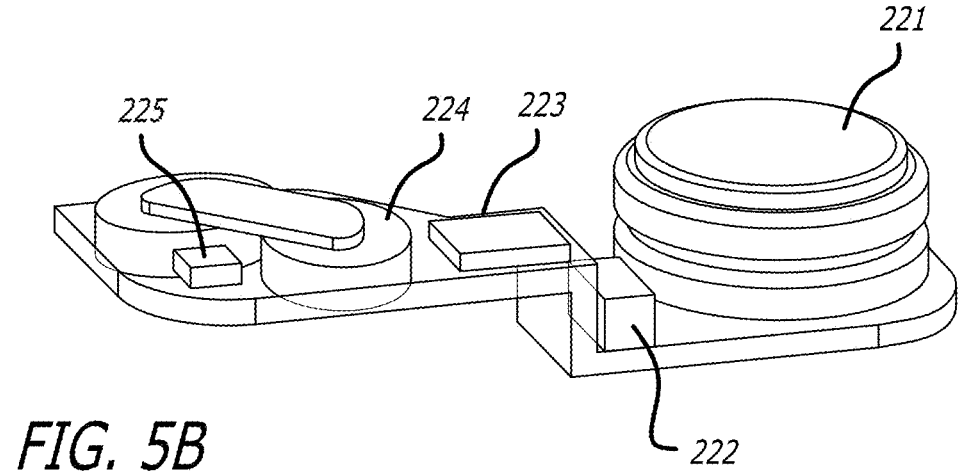
FIG. 5B is a perspective view of the components of the exemplary durable assembly illustrated in FIG. 5A.
Figure 5C:
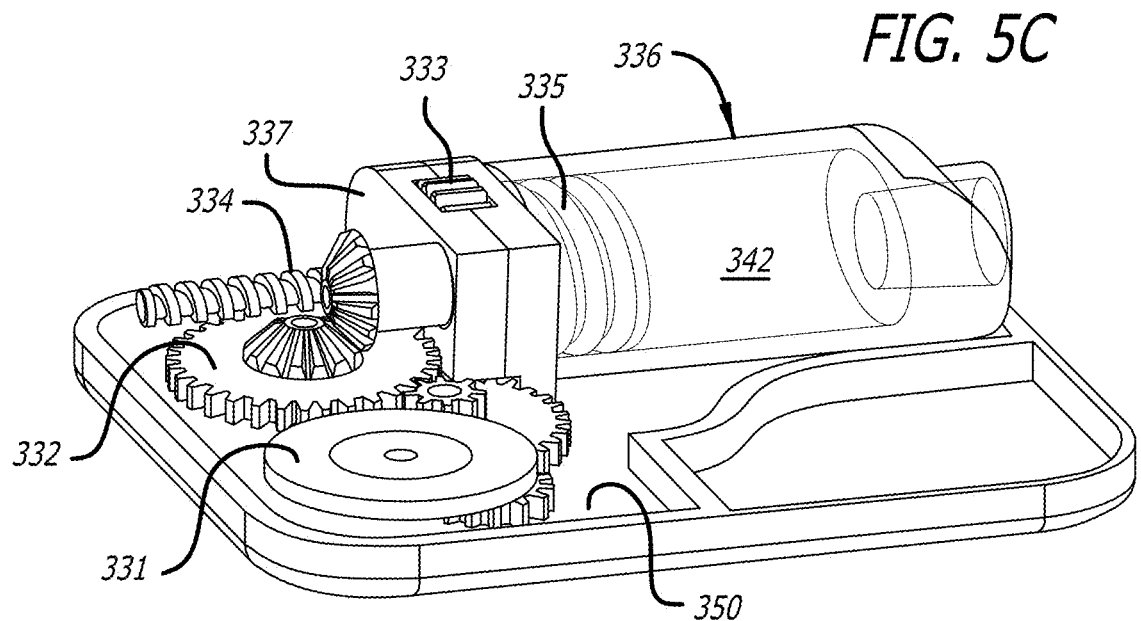
FIG. 5C is a perspective view of the components of the exemplary disposable assembly illustrated in FIG. 5A.

Turning now to FIGS. 5A-5C and the illustrated two-piece motor, the motor's coil assembly 224 (and a Hall-effect sensor 225) of the durable assembly 200 are positioned above the magnetic motor rotor 331 that is part of the disposable assembly 300. An exemplary multi-pole motor rotor 331 may be disc-shaped and have a 9.8 mm outer diameter, 5.2 mm inner diameter, and 0.8 mm thickness. Another example motor rotor may have an 11 mm outer diameter, 5 mm inner diameter, and 1.2 mm thickness. Multi-pole motor rotors of this type typically cost less than 5 cents per piece, helping control the total cost of disposable assembly 200. The motor rotor 331 is also parallel to the baseplate 350, i.e., the motor rotor axis of rotation is perpendicular to the baseplate, in the illustrated embodiment. The microprocessor 223 directs rotation of motor rotor 331 by sequentially energizing the coils of motor coil assembly 224 to create an electromagnetic torque coupling between the motor coil assembly 224 and the motor rotor 331. The position/orientation of the rotor's poles relative to the rotating magnetic field generator (coil assembly 224) is measured by back EMF, a rotary encoder, a Hall-effect sensor 225 (FIG. 5A), or the like. For instance, a Hall-effect sensor mounted on the coil windings may be used to supply the microprocessor a count, a tachometer signal, or rotor position, allowing low-cost closed-loop control of the rotor speed. Brushless motors of this type are typically 85-90% or more efficient, and run very cool. While there may be variations in construction, the face-to-face stator coils and flat rotor plate shown in FIGS. 5A-5C provide a compact design. In addition, more coils and/or Hall-effect sensors may be used.

Figure 6:
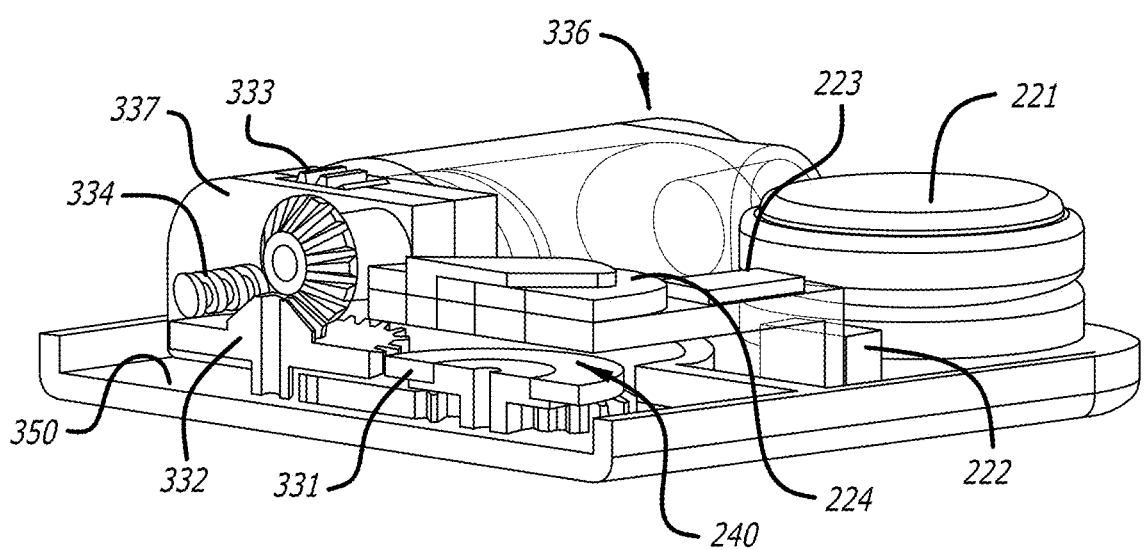
FIG. 6 is a perspective section view of components of the exemplary infusion pump system of FIG. 5A, revealing a gap between certain components of the durable and disposable assemblies.

As can best be seen in FIG. 6, between the motor coil assembly 224 and motor rotor 331 is a gap 240. Some or all of the gap 240 may be defined by (and occupied by) portions of the housing 202 and the cover 302, i.e., the housing bottom wall 206a and the cover top wall 304b in the illustrated implementation. In other implementations, the gap 240 between the motor coil assembly 224 and motor rotor 331 may be occupied by only a portion of the durable assembly housing, or only a portion of the disposable assembly cover, or no structure at all and may simply be an air gap. The size of the gap, which is defined by the distance between the motor coil assembly 224 and the motor rotor 331, is typically about 0.5 mm to 2.0 mm. As such, there is no gear engagement or other mechanical connection between the durable assembly 200 and disposable assembly 300. And as described earlier, all electronics may be positioned within the durable assembly 200, with the energy needed by the disposable assembly 300 transferred by electromagnetic torque coupling, which is a coupling without direct mechanical coupling or electrical contact from the durable assembly 200. This exemplary design affords the additional advantage of being relatively simple to make waterproof, or at least water resistant.

As described above, rotation of motor rotor 331 drives gear train 332, causing rotation of lead screw drive gear 333, which in turn affects translation of the lead screw 334 and plunger 335, which is attached to lead screw 334. In this manner, electromagnetically generated torque is created when electromagnetic energy supplied by durable assembly 200 is transformed into mechanical forces within the disposable assembly 300 that advance plunger 335. A ratchet (not shown) or other similar device may be used to prevent back-driving of gear train 332. As plunger 335 is driven through reservoir 336, medicament is dispensed precisely, corresponding to the precision movements of the gears and motor rotor. With the entire gear train, lead screw drive gear, lead screw, and plunger all permanently contained in the disposable assembly 300, there is no need to retract any plunger components into the durable assembly 200 before separation from the disposable assembly 300. As a result, a further advantage of this exemplary design (and those below) is greatly reduced energy consumption, which allows use of, for instance, a primary battery(ies) as a power source.

Figure 8:
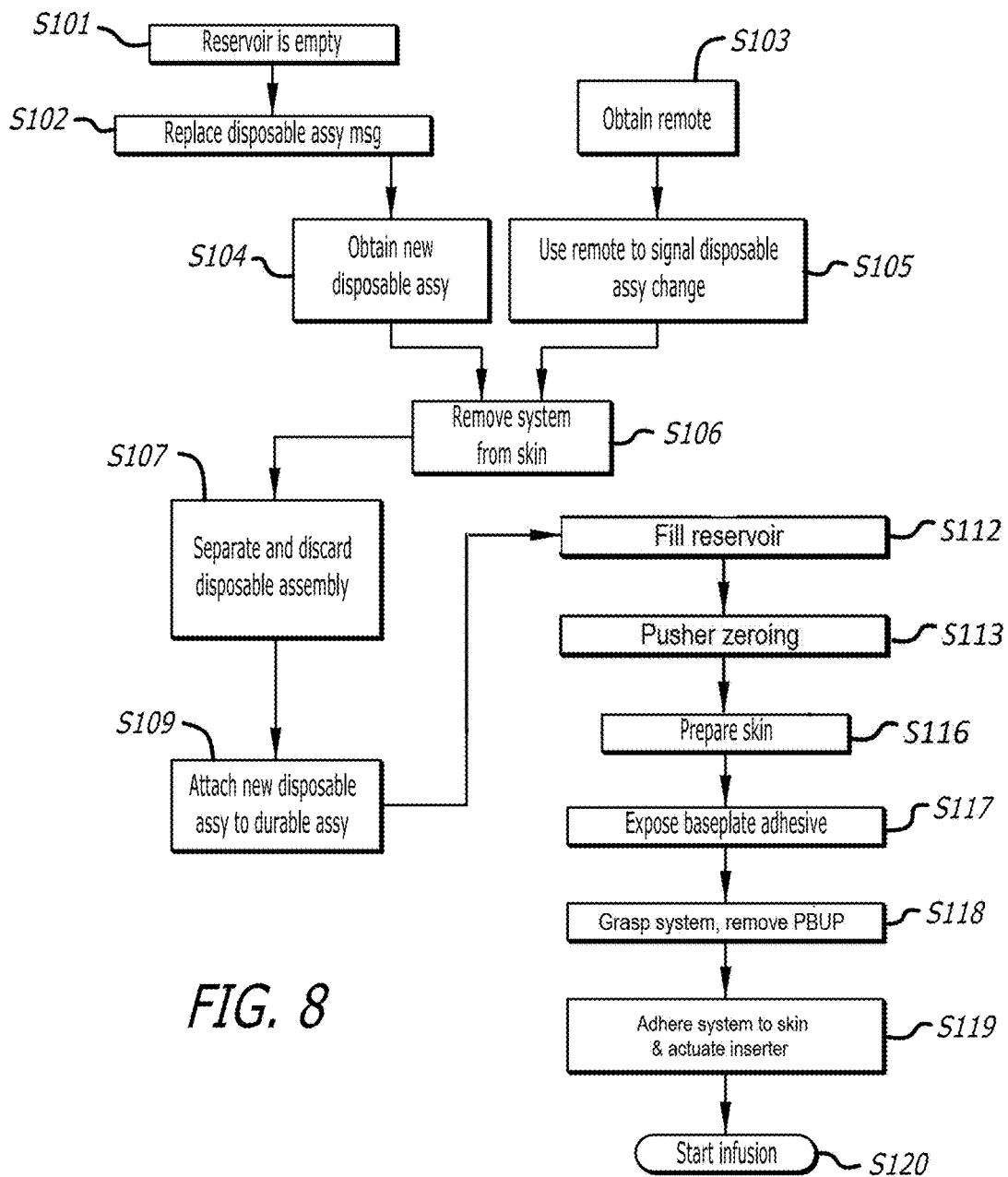
FIG. 8 is a flow chart illustrating an exemplary disposable assembly removal and replacement method.

Use of an exemplary system 100 will now be described. At the most basic level, a patient's use of the exemplary infusion pump systems (e.g., system 100 in FIGS. 1A-2B) involves obtaining a new disposable assembly 300, connecting the disposable assembly to the durable assembly 200, peeling the liner from the baseplate adhesive layer, gaining subcutaneous access, and initiating a medicament delivery operation. In some instances, use may involve additional steps such as attaching a cannula to connector 380 of the disposable assembly and removing a cannula cap, if necessary. Various aspects of the basic operation of the present systems are described below. Operation of a system does not necessarily require all the steps each time the system is deployed, and the order of some of the steps may be changed. Operation is also discussed below, in the exemplary context of the above-described durable assembly 200 and disposable assembly 300 used as a patch pump, via a flow chart (FIG. 8). The discussion is, however, equally applicable to other patch pump implementations, such as described in FIGS. 10A-10H, as well as to pocket pump implementations with minor variations. Also, unless otherwise indicated, the actions and determinations performed by the durable assembly 200 are controlled by the durable assembly microprocessor and further references to the controller are limited in the interest of brevity.

Referring to FIG. 8, use of the present systems may involve removal of a disposable assembly from a durable assembly and the replacement of the disposable assembly. This may occur when the medicament reservoir is empty (as described in more detail in U.S. patent application Ser. No. 12/890,207 and corresponding U.S. Pat. No. 8,777,901) (Step S101) and a "replace disposable assembly" message or alert is presented on remote control 1000 (Step S102), or when a buzzer or other alarm (audible, palpable, visible or combinations thereof) from the durable or disposable assembly may signal the need for disposable assembly replacement. Alternatively, the durable assembly controller may receive a user-initiated "replace disposable assembly" signal from a remote control 1000 (Step S103). The user may desire to replace a disposable assembly before the medicament reservoir is empty for a variety of reasons such as, for example, to accommodate the user's sleep or travel schedule, when the medicament exhibits a loss of effectiveness, when a dispensing problem arises, or due to a prescribed change in medicament The user may then obtain, possibly from storage in a refrigerator depending on medicament requirements, a new pre-filled disposable assembly 300 or may then obtain a new disposable assembly and fill the reservoir in the disposable assembly with medicament (Step S104). Alternatively, the reservoir may be filled after the disposable assembly 300 is attached to durable assembly 200, as described below. The durable assembly 200 and disposable assembly 300 may then be removed from the skin, separated, and the used disposable assembly 300 discarded (Steps S106 and S107).

Figure 7:
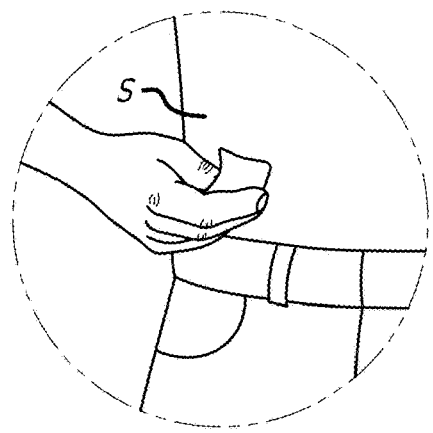
FIG. 7 is a front view showing a patient's skin being cleaned.

Next, the new disposable assembly 300 may be attached to the durable assembly 200 (Step S109). In the case of disposable assemblies with user-filled reservoirs, if not filled earlier, the user then injects medicament from a syringe into the reservoir (Step S112). Medicament may be injected until the reservoir is full, or the user may choose to introduce a specific amount of medicament from the syringe. Since an unknown amount of medicament may be injected into a user-filled reservoir, a plunger-pusher zeroing procedure (Step S113), such as described in U.S. patent application Ser. No. 12/890,207, and corresponding U.S. Pat. No. 8,777,901, may then be user-initiated or may be an automatic aspect of pump operation. If the results of the zeroing procedure are negative, the disposable assembly 300 may be removed and discarded, a new disposable assembly attached and filled, and the zeroing procedure repeated. A slightly altered zeroing procedure is described in more detail below In either a user-filled or pre-filled configuration, the user should then clean the skin surface S onto which the baseplate 350 of disposable assembly 300 will be adhered (FIG. 7, and Step S116 of FIG. 8). Then the user peels off the baseplate adhesive liner to expose the baseplate adhesive layer (Step S117) and removes the pull-before-use plug, PBUP 517, when present (Step S118). These last two steps S117 and S118 may be performed in reverse order, as required or desired The system 100 including durable assembly 200 and disposable assembly 300 may be positioned over the chosen body location and pressed gently to adhere the adhesive layer to the skin surface S. Once the system has been adhered, the inserter may be actuated (Step S119), as described in more detail below, to position the end of a cannula about 6 mm below the skin. Finally, if necessary, the remote control 1000 may be used to initiate a particular medicament delivery operation (Step S120). The delivery operation may follow a predetermined delivery profile (e.g. a particular basal rate, a series of time-spaced bolus deliveries, or some combination thereof) that is equated to motor rotor rotations, at particular rates and times, required to deliver medicament in accordance with the profile. Alternatively, the profile may be input by the user with the remote control 1000 and stored by the durable assembly microprocessor. For example, the remote control may store a number of different delivery profiles and bolus deliveries from which the patient can choose. Such profiles may correspond to, for example and depending on the medicament, days where vigorous exercise is expected, days where it is not, incidences of increased pain, etc. Alternatively, or in addition, the profile stored in the durable assembly microprocessor may be set by a clinician's programming unit. In such a case, as in the case of different disposable assemblies 300 provided with different specified delivery rates, a remote control may not be needed to initiate, e.g., basal delivery.

The discussion above is also applicable to use of the "pocket pump" system as shown in FIG. 2B. Minor variations in the above-described procedure include, for example, use of an infusion set 382 instead of a cannula, attaching the infusion set to connector 380, potentially via an adapter (which may vary with the type of infusion set 382), and priming of the tube of infusion set 382.

Figure 9A:
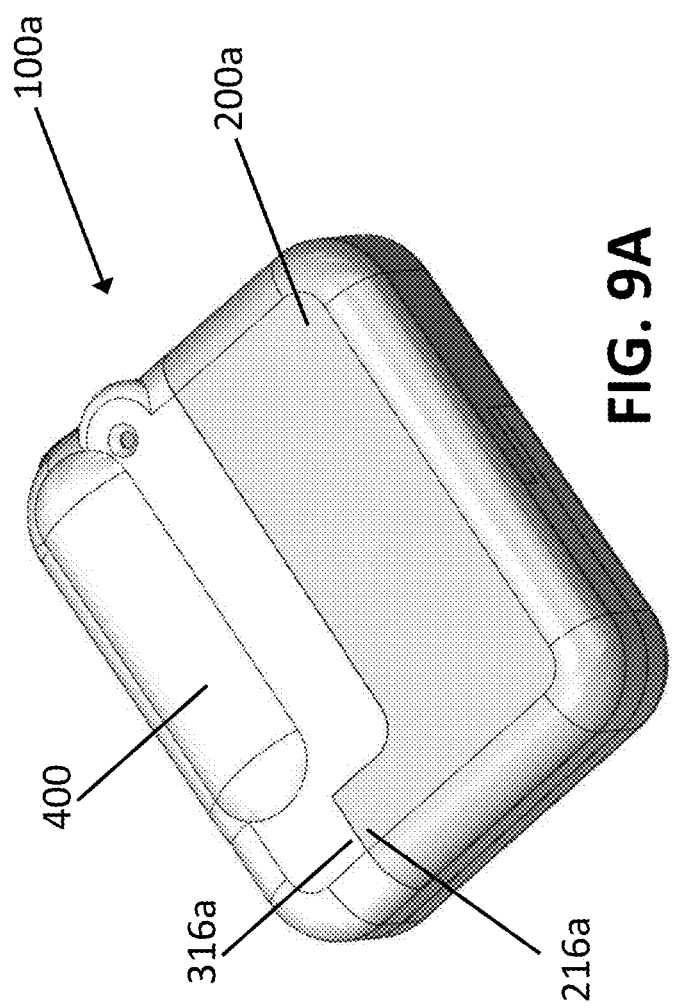
FIG. 9A is a perspective view of another exemplary infusion pump system in an assembled state.

Another exemplary ambulatory infusion system, which is generally represented by reference numeral 100a in FIG. 9A, includes a durable assembly 200a and a disposable assembly 400. System 100a is substantially similar to system 100. Here, however, the intersection of the top walls is primarily linear. Additionally, the disposable assembly 400 has a recess 316a which mates with a corresponding projection 216a on the durable assembly 200a. The projection 216a and recess 316a are located at the outer perimeter of the assembled system 100a.

Figure 9C:
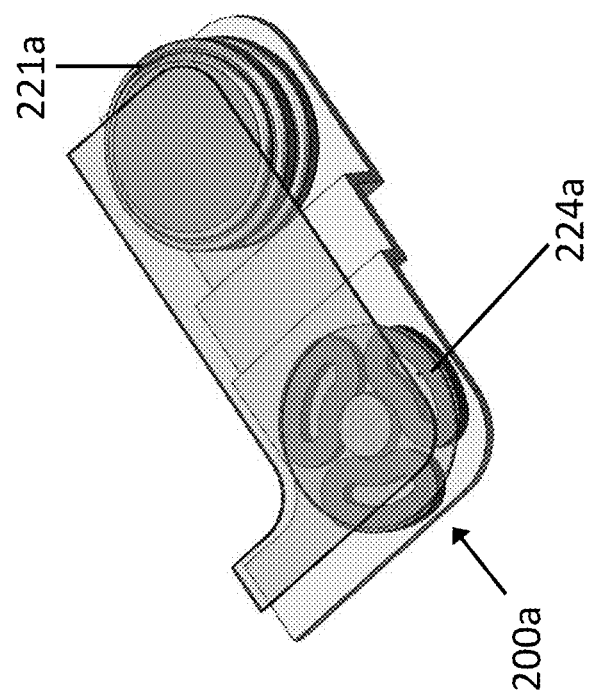
FIG. 9C is a perspective view of certain components of the durable assembly illustrated in FIG. 9.
Figure 9B:
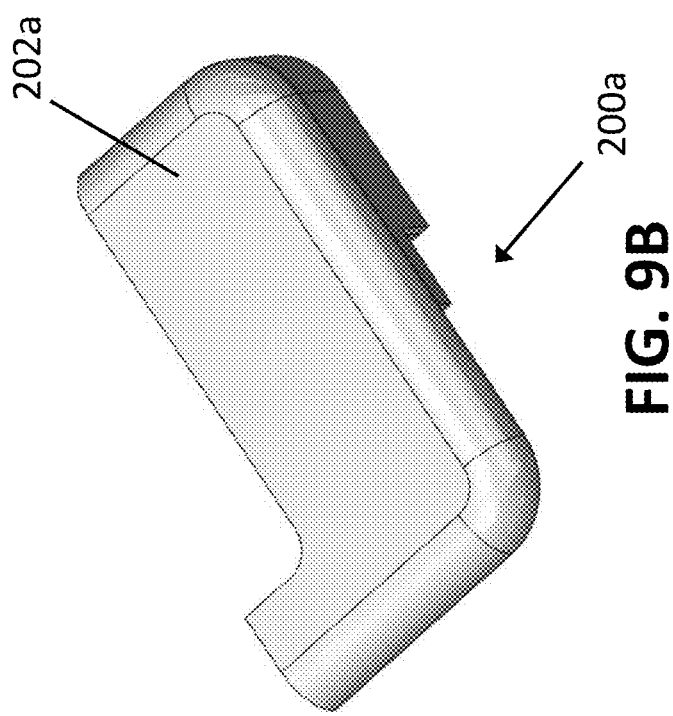
FIG. 9B is a perspective view of an exemplary durable assembly of the infusion pump system of FIG. 9A.
Figure 9D:
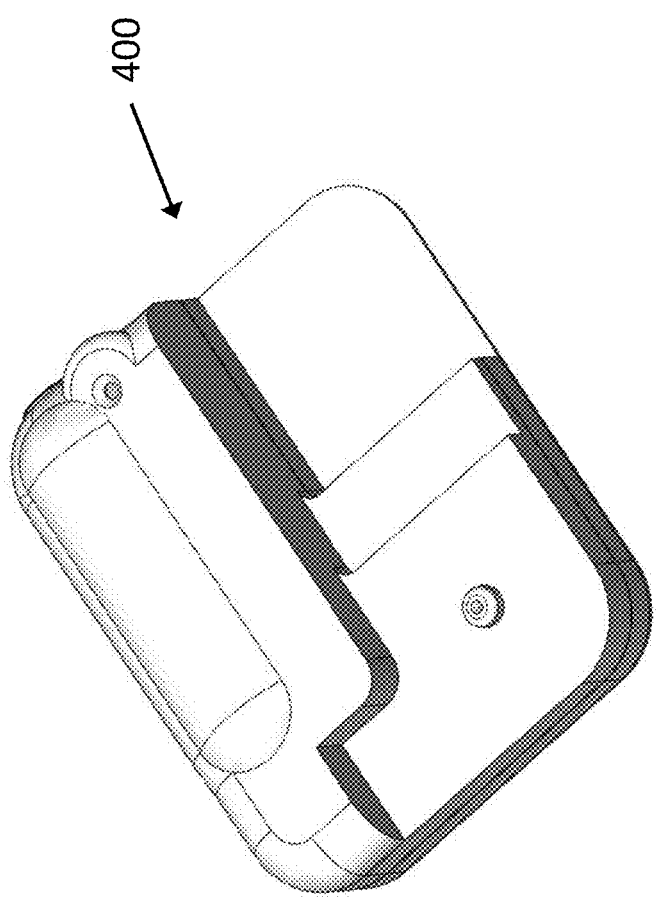
FIG. 9D is a perspective view of an exemplary disposable assembly of the infusion pump system of FIG. 9A.
Figure 9E:
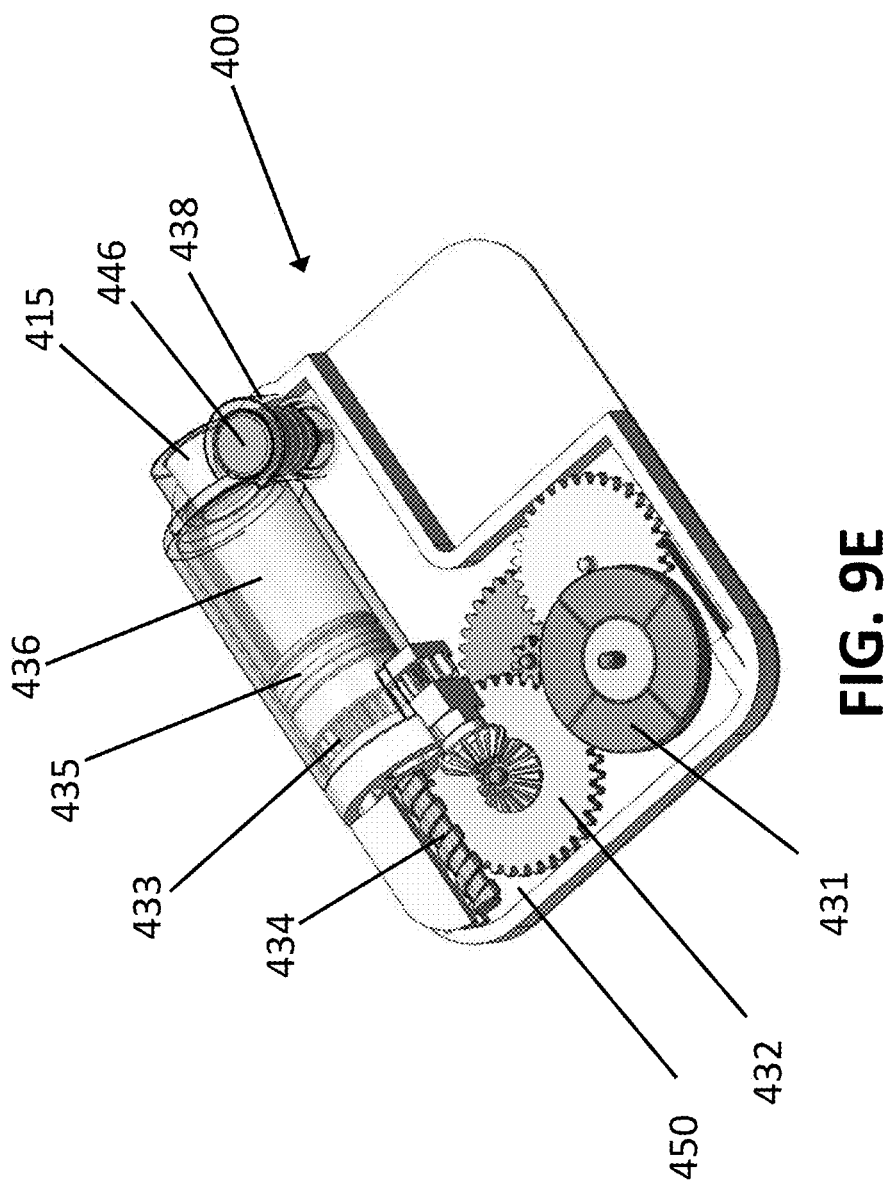
FIG. 9E is a perspective view of certain components of the disposable assembly illustrated in FIG. 9D.

Exemplary durable assembly 200a, shown in more detail in FIGS. 9B and 9C, may include a housing 202a, one or more batteries or other energy supply 221a, one or more capacitors or other energy storage (not shown), a microprocessor (not shown), and a coil assembly 224a including one or more Hall-effect sensors (not shown). Exemplary disposable assembly 400, shown in more detail in FIGS. 9D and 9E, may include a baseplate 450 supporting components such as a magnetic motor rotor 431, a gear train 432 including lead screw drive gear 433, and a lead screw 434 attached to plunger assembly 435 which is positioned in a medicament reservoir 436 having a circular cross-section. The magnetic motor rotor 431 may be mechanically attached through gear train 432 to affect rotation of the lead screw drive gear 433, which causes translation of the lead screw 434 and the plunger 435 within reservoir 436. Reservoir 436 may be, for instance, prefilled with U-500 insulin or U-100 insulin or other concentrations of insulin to suit different patient use profiles, or may be user-fillable via a fill port 415. A reservoir outlet 438 is in fluid communication with reservoir 436. Disposable assembly 400 may be secured to durable assembly 200a, as shown in FIG. 9A and as further described in U.S. provisional patent application Ser. No. 62/057,273, corresponding U.S. patent application Ser. No. 14/869,906, and corresponding U.S. patent publication number 2016/0089491.

Figure 10A:
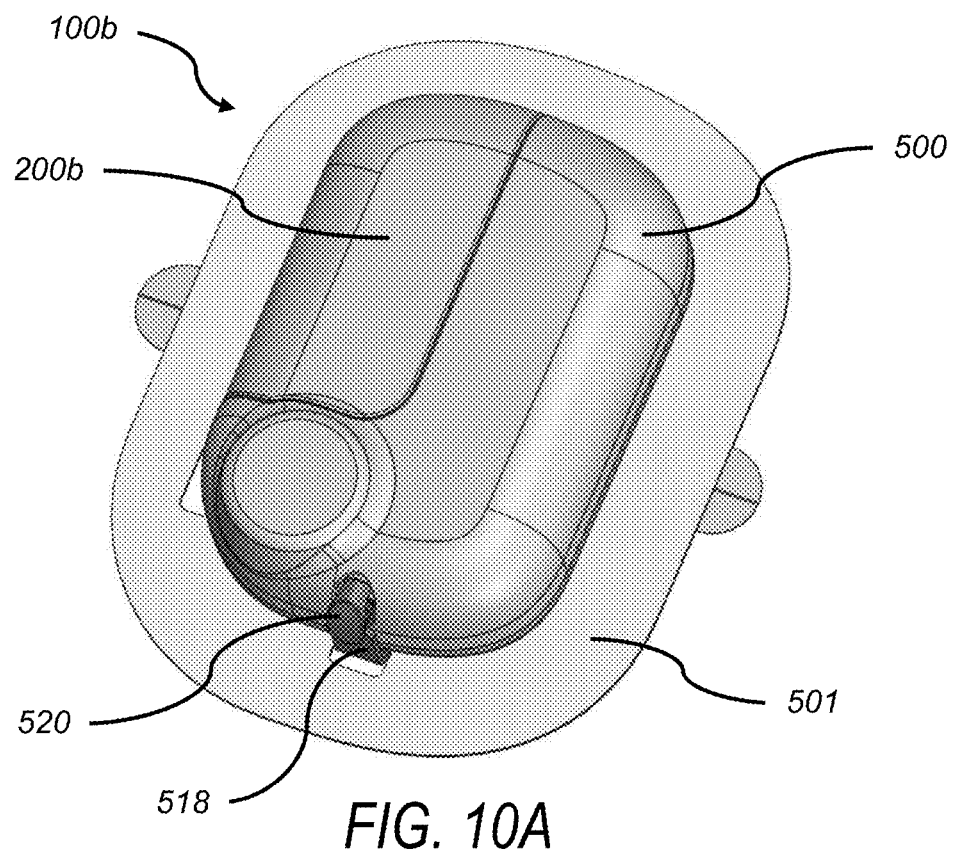
FIG. 10A is a perspective view of another exemplary infusion pump system, shown in assembled state one, before pull-before-use plug, PBUP 517, is removed.
Figure 10B:
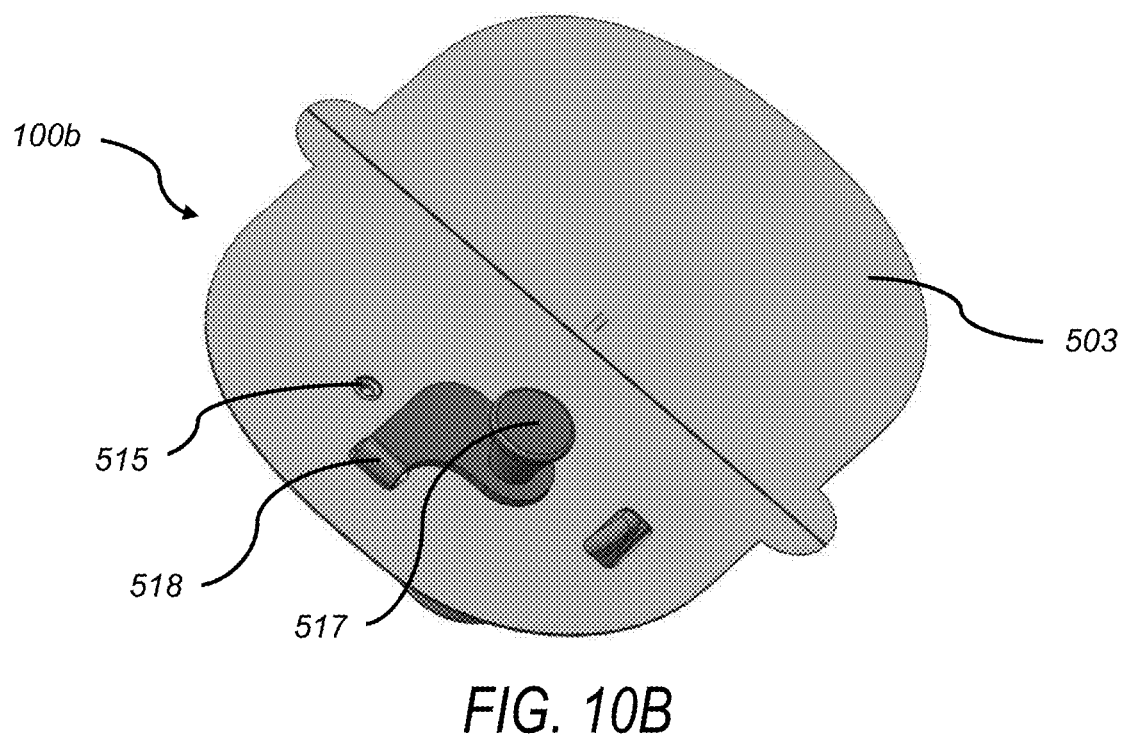
FIG. 10B is a perspective view of the bottom of the infusion pump system of 10A.

Another exemplary ambulatory infusion system, which is generally represented by reference numeral 100b in FIGS. 10A and 10B, includes a durable assembly 200b and a disposable assembly 500. System 100b is substantially like systems 100 and 100a. Here, the intersection of the top and inside walls is linear in places and curved in others. Also shown in FIGS. 10A and 10B are adhesive pad 501 with adhesive backing 503 attached, fill port 515, pull-before-use plug (PBUP) 517, and cannula trigger button 520. These features are described in more detail below.

Figure 10C:
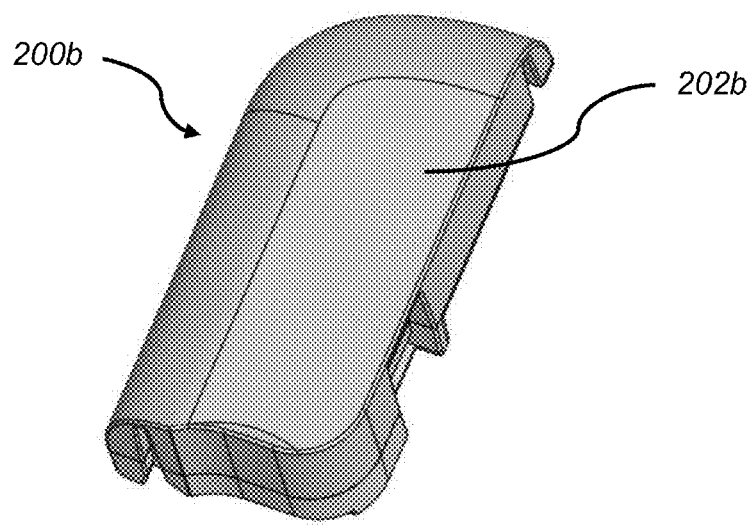
FIG. 10C is a perspective view of an exemplary durable assembly of the infusion pump system of FIGS. 10A and 10B.
Figure 10D:
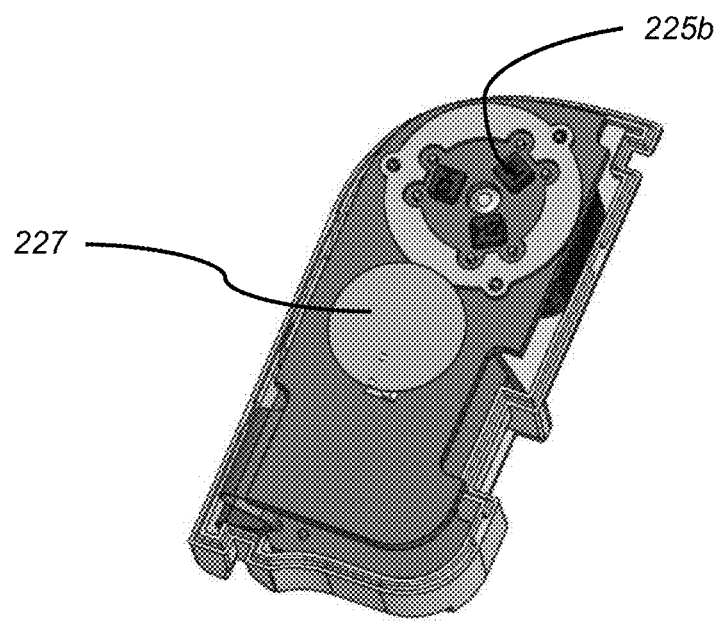
FIGS. 10D and 10E are perspective views of certain components of the durable assembly illustrated in FIG. 10C.
Figure 10E:
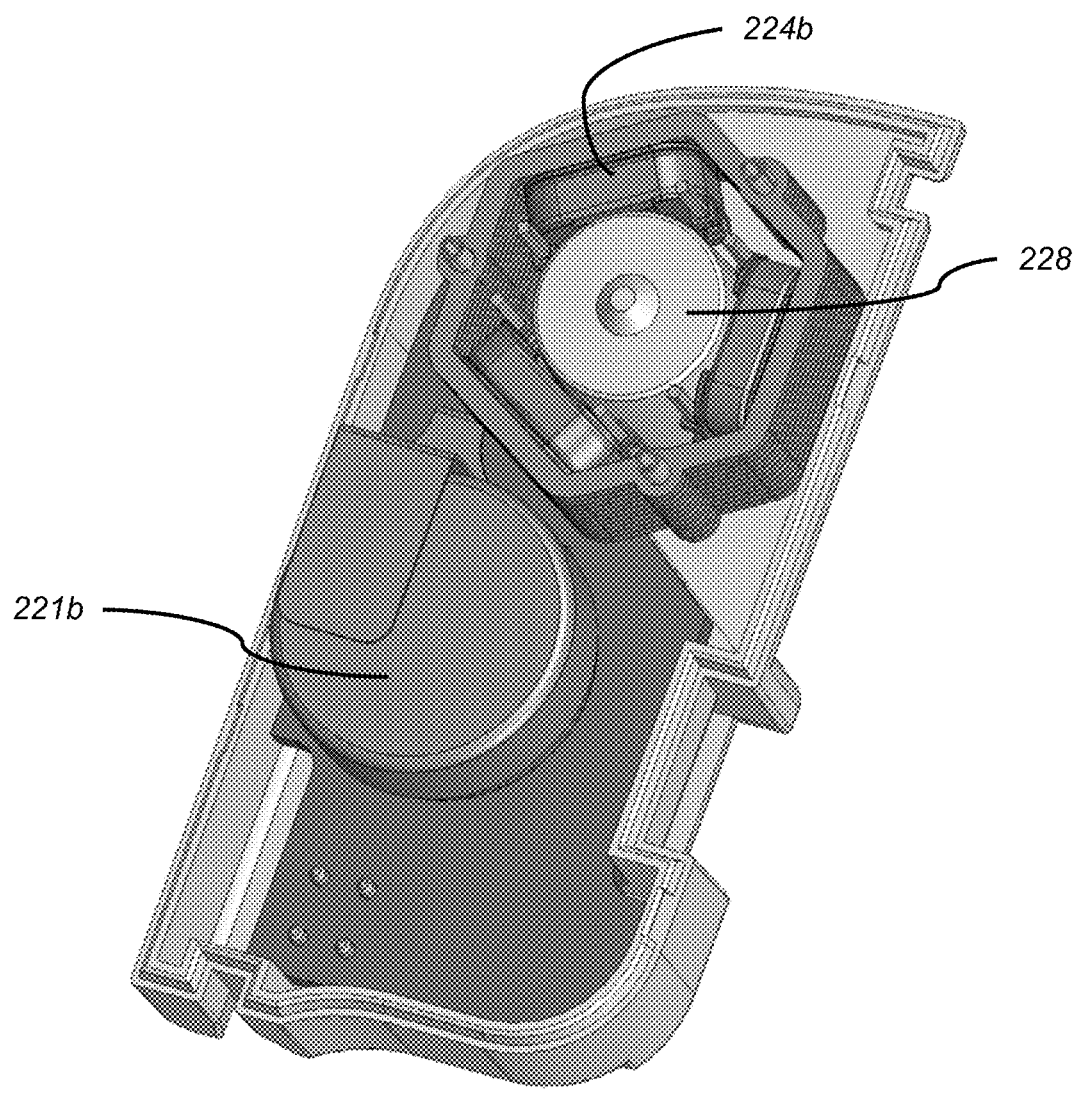

Exemplary durable assembly 200b, shown in more detail in FIGS. 10C-10E, may include a housing 202b, a buzzer or other alarm device 227, one or more batteries or other energy supply 221b, a microprocessor (not shown), and a coil assembly 224b (which functions as a motor stator) including one or more Hall-effect sensors 225b. In this embodiment, energy supply 221b is a rechargeable battery, such as a rechargeable lithium battery, with enough power to drive the motor continuously without needing a capacitor or other additional energy storage device. As mentioned earlier, exemplary durable assembly microprocessors and associated circuitry; rechargeable batteries and associated battery rechargers and recharging methods; battery and recharging management; temperature sensors; and exemplary alarms and alarm conditions are described in more detail in aforementioned U.S. Pat. Nos. 8,777,901; 8,905,972; and 9,114,208.

Figure 10F:
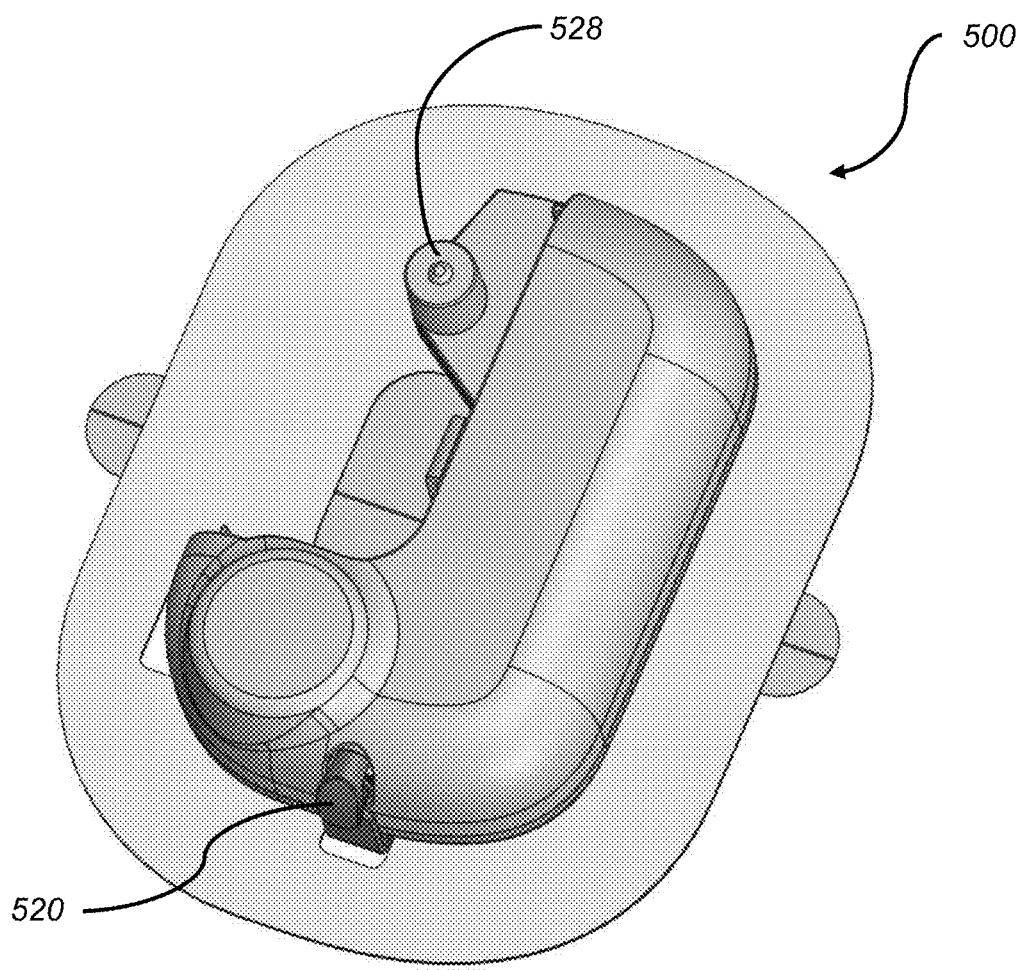
FIG. 10F is a perspective view of an exemplary disposable assembly of the infusion pump system of FIG. 10A.
Figure 10G:
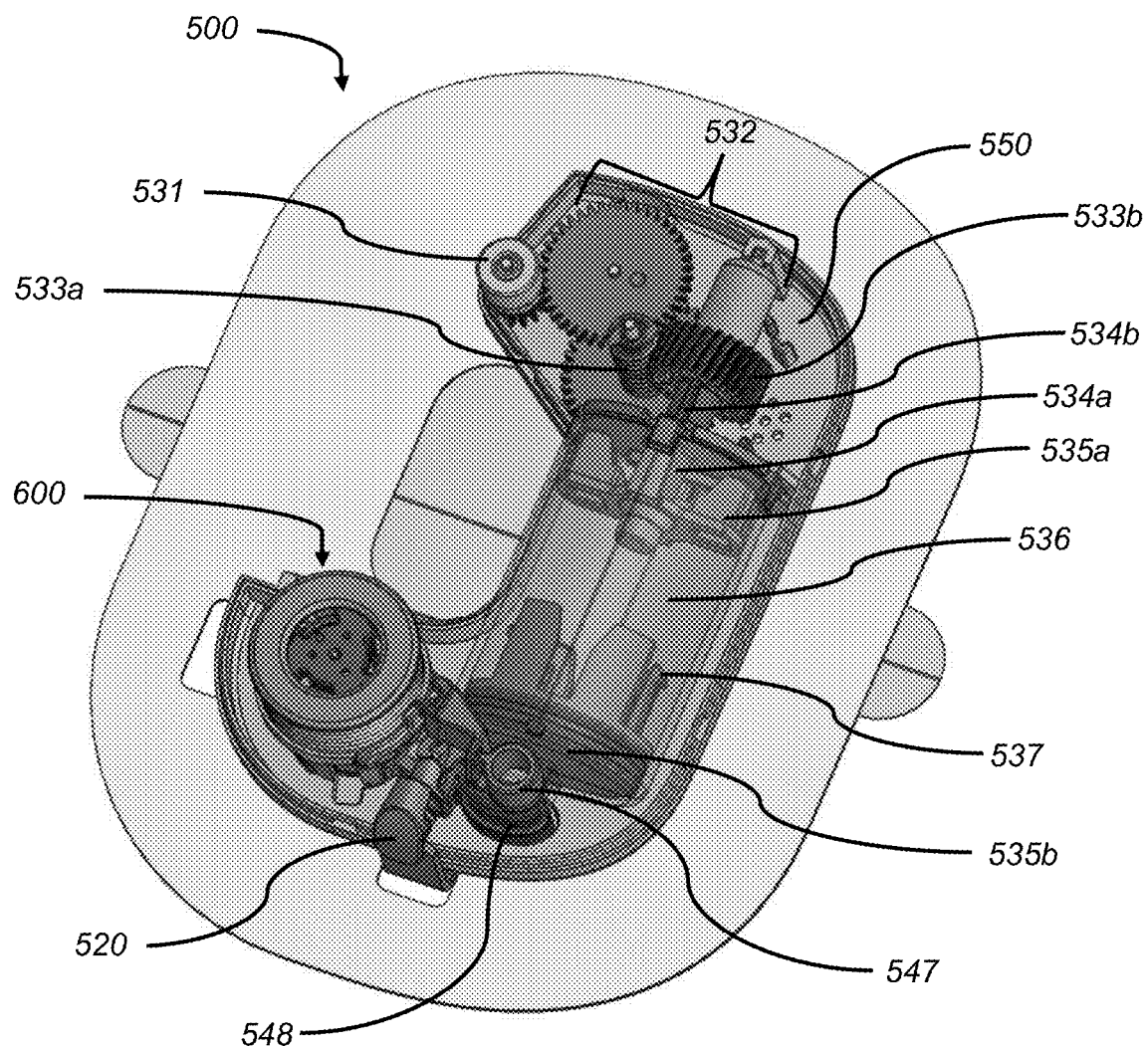
FIG. 10G is a perspective view of certain components of the disposable assembly illustrated in FIG. 10F.

Returning to FIG. 10E, coil assembly 224b is positioned around durable housing portion 228, which is configured to fit over disposable housing portion 528 (FIG. 10F), which in turn fits over magnetic motor rotor 531 (FIG. 10G). In this two-piece motor, the motor's coil assembly 224b is in durable assembly 200b and is positioned around motor rotor 531 that is part of the disposable assembly 500. Hall-effect sensors 225b are positioned above coil assembly 224b in durable assembly 200b. In this configuration, there is a gap between motor coil assembly 224b and motor rotor 531. Some or all of the gap may be defined by (and occupied by) housing portions, e.g., durable housing portion 228 and disposable housing portion 528 in the illustrated implementation. In other implementations, the gap between the motor coil assembly 224b and motor rotor 531 may be occupied by only a portion of the durable assembly housing, or only a portion of the disposably assembly cover, or no structure at all and may simply be an air gap. The size of the gap, which is defined by the distance between the motor coil assembly 224b and the motor rotor 531, is typically about 0.5 mm to 2.0 mm. As such and as described earlier, there is no gear engagement or other mechanical connection between the durable assembly 200b and disposable assembly 500. Also as described earlier, all electronics may be positioned within the durable assembly 200b, with the energy needed by disposable assembly 500 transferred by electromagnetic torque coupling, which is a coupling without direct mechanical coupling or electrical contact from the durable assembly 200b. These exemplary designs afford the additional advantage of being relatively simple to make waterproof, or at least water resistant.

An exemplary motor rotor 531 may be a 2-pole, cylinder-shaped, rare earth (such as neodymium) rotor, magnetized across the diameter, with a 5 mm diameter and 5 mm height. Other suitable motor rotors may be larger or smaller, or be multi-pole. Motor rotors of this type typically cost about 5 cents per piece, helping control the total cost of disposable assembly 500. The microprocessor (not shown) directs rotation of motor rotor 531 by sequentially energizing the coils of motor coil assembly 224b to create an electromagnetic torque coupling between the motor coil assembly 224b and the motor rotor 531. The position/orientation of the rotor's poles relative to the rotating magnetic field generator (coil assembly 224b) is measured by back EMF, a rotary encoder(s), one or more Hall-effect sensors 225b, or the like. For instance, the Hall-effect sensors 225b mounted above the coil windings 224b may be used to supply the microprocessor a count, a tachometer signal, or rotor position, allowing low-cost, closed-loop control of the rotor speed. As stated earlier, brushless motors of this type are efficient and run very cool. While there may be variations in construction, the configuration shown in FIGS. 10D-10G provides a compact design.

Exemplary disposable assembly 500, shown in more detail in FIGS. 10F and 10G, may include a baseplate 550 supporting components such as above-described magnetic motor rotor 531 and a gear train 532. Gear train 532 is attached to a plunger assembly 535 that is positioned in a medicament reservoir 536. Plunger assembly 535 comprises, among other items, plunger pusher 535a and plunger 535*b*. The magnetic motor rotor 531 may be mechanically attached through gear train 532 to affect translation of plunger pusher 535*a* (and plunger 535*b*, when attached to plunger pusher 535*a*) within reservoir 536. Reservoir 536 may be, for instance, prefilled with U-100 insulin or U-500 insulin or other concentrations of insulin to suit different patient use profiles, or may be user-Tillable by way of a fill port 515. A reservoir outlet fitting 548 is in fluid communication with reservoir 536. A cannula trigger button 520, when pressed, causes rotation of a trigger link 547 that is positioned above reservoir outlet fitting 548, triggering cannula insertion (as described in more detail below). Reservoir outlet fitting 548 is made from a drug-compatible material, such as, but not limited to, polypropylene, cyclic olefin polymer (COP) or polyethylene. Cannula trigger button 520 and trigger link 547 may be made of a strong, lightweight material, such as polycarbonate, nylon, acetal (Delrin®) or the like. Disposable assembly 500 may be secured to durable assembly 200*b*, as shown in FIG. 10A and as further described above or in aforementioned U.S. patent publication number 2016/0089491.

As best seen in FIG. 10G, gear train 532 of exemplary disposable assembly 500 is slightly different from the gear trains in the embodiments described above. In this embodiment, gear train 532 includes a worm drive comprised of worm screw 533*a* and worm gear 533*b*, and also a fine-pitch lead screw (not shown) and lead screw nut 534*a*. The worm gear 533*b* is coupled to the lead screw via the lead screw nut 534*a*, which encloses the lead screw. Protrusions 534*b* on the lead screw nut 534*a* correspond with recesses (not shown) inside worm gear 533*b*, and a threaded portion (not shown) inside lead screw nut 534*a* pairs with the thread on the lead screw enclosed by the lead screw nut 534*a*. The configuration of gear train 532 prevents back-driving, eliminating the need for a clutch or other locking mechanism. Suitable materials for the components of gear train 532 include, but are not limited to, stainless steel or high strength plastic, such as nylon, acetal (Delrin®) or polycarbonate.

As also seen in FIG. 10F, exemplary disposable assembly 500 also differs from the above embodiments in that plunger assembly 535 includes a plunger pusher 535*a* in addition to a plunger 535*b*. Exemplary infusion pumps that include a reservoir with a plunger in combination with a fluid displacement device in the form of a plunger pusher are described in aforementioned U.S. Pat. No. 8,777,901. In the case of disposable assemblies with user-filled reservoirs, the user may completely fill the reservoir to capacity with medicament, or the user may choose to introduce less medicament, and not completely fill the reservoir. As described earlier, since an unknown amount of medicament may be injected into a user-filled reservoir, a plunger-pusher zeroing procedure, such as described in U.S. Pat. No. 8,777,901, may be user-initiated or may be an automatic aspect of pump operation. The pusher zeroing procedure precisely determines and/or sets, before any medicament dispensing, exactly how far plunger pusher 535*a* must travel before it engages plunger 535*b*, allowing a calculation to determine the amount of medicament in the reservoir and, therefore, an estimate of time-to-empty and need for disposable assembly replacement.

Figure 10H:
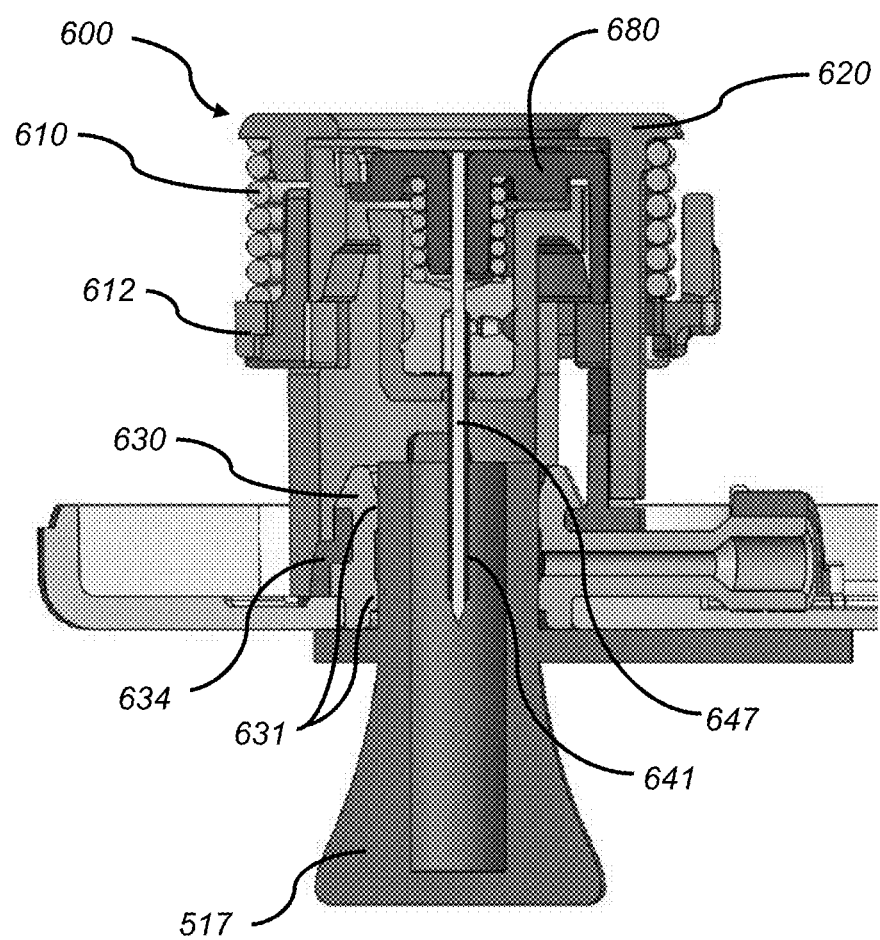
FIG. 10H is a section view showing certain components of the disposable assembly illustrated in FIG. 10G, shown in state one.

FIG. 10G shows the plunger assembly 535 before any medicament is introduced into reservoir 536. At this point, and until pusher zeroing is complete, plunger 535*b* is free-floating within reservoir 536, and PBUP 517 must be in place, as shown in FIG. 10H. Plunger pusher 535*a* is, at all times, attached to lead screw 534*a*, and begins in the fully-retracted position. As medicament is introduced into reservoir 536 via fill port 515, plunger 535*b* is pushed towards plunger pusher 535*a*. If the reservoir is filled to capacity, plunger 535*b* will be pushed into contact with plunger pusher 535*a*, causing hooks 537 (or other suitable method of attachment) on pusher 535*b* to engage with and permanently lock pusher 535*b* to plunger pusher 535*a*. If reservoir 536 is not filled to capacity, plunger 535*b* will be positioned at some unknown point within reservoir 536 until plunger zeroing is complete. Once the user has introduced medicament into reservoir 536, plunger zeroing is user-initiated or may be an automatic aspect of pump operation (e.g., when disposable assembly 500 is attached to a durable assembly). When the pusher-zeroing procedure is initiated, the motor advances plunger pusher 535*a* until it contacts pusher 535*b*, and they lock together with plunger hooks 537, or other suitable method of attachment, as described earlier. Reservoir 536 and plunger 535*b* may be made of cyclic olefin polymer (COP), polypropylene or other drug-compatible polymeric material. Suitable materials for the plunger pusher 535*a* include, but are not limited to, stainless steel, COP, nylon, and polycarbonate.

As described earlier, the zeroing procedure is performed when flow from cartridge 536 is blocked by PBUP 517. Given there may be tolerances associated with cartridge manufacture and variation in medicament filling, the distance that plunger pusher 535*a* must travel, from its initial home position, before it engages plunger 535*b* and begins to drive medicament out of the reservoir, may vary. Under microprocessor control, the motor advances plunger pusher 535*a* into engagement with plunger 535*b*, causing increased fluid path pressure. The Hall-effect sensors 225*b*, an encoder, or other monitoring/sensing device is sampled to determine when a motor stall occurs as pusher 535*a* is advanced. Lack of signals from the Hall-effect sensors 225 evidences that the motor is not turning. The motor stall is presumed to be due to hydraulic lock and, therefore, indicative of plunger pusher 535*a* engaging the plunger 535*b* of a plugged cartridge 536. As described in detail in aforementioned U.S. Pat. No. 8,777,901, the procedure may employ two or more speeds for advancing the pusher. Also, pusher 535*a* may be advanced at a controlled torque, or limited force, so that the motor will stall with the least amount of force possible for reliable results, in order to reduce the load on the system (e.g., the bearings and the battery). As stated above, knowing the distance plunger pusher 535*a* traveled before engaging plunger 535*b* allows calculations of medicament volume and estimated time until disposable assembly 500 replacement will be required.

Insertion mechanism 600 is a 4-state system. FIGS. 10A-10H show insertion mechanism 600 in its first state: the cocked position, before the patient removes PBUP 517 (FIG. 10H) and pushes cannula trigger button 520 (FIG. 10G) to insert the cannula. In this state, PBUP 517 is positioned to occlude the fluid path from the reservoir 536 (FIG. 10G) and cannula carrier 612 is held up above and spaced apart from cannula seal 630 (FIG. 10H), as described further below. In this state, and as best seen in FIG. 10G, the plunger-pusher zeroing procedure described above can advance the pusher 535*a* into contact with the plunger 535*b*, slightly pressurizing the reservoir 536, without injecting medicament into the patient. As best seen in FIG. 10H, seal is formed between seal rings 631 and the outer surface of PBUP 517, allowing the pressures required for the plunger-pusher zeroing procedure.

To prevent accidental depression of cannula trigger button 520, a button guard may be inserted between button 520 and the housing of disposable assembly 500. For instance, as best seen in FIGS. 10A and 10B, PBUP 517 may include a trigger button guard 518 that curves up from the underside of infusion system 100b through an opening in adhesive pad 501, and fits under cannula trigger button 520. With button guard 518 in place, it is not possible to depress trigger button 520 to initiate cannula insertion. PBUP 517 may be made of COP, polypropylene or other similar drug-compatible material. Button guard 518 may be made of the same material as PBUP 517 (and they may be one piece), or it may be made of a different material, such as polycarbonate.

Turning now to FIGS. 11A-11D, exemplary disposable assembly 500 includes baseplate 550, reservoir outlet fitting 548, and insertion mechanism 600, shown with cannula trigger button 520 and trigger link 547 removed for clarity. As can be seen from these and the earlier figures, infusion system 100b (and all infusion systems shown in the figures) is extremely compact, limiting available spring energy and the volume available for the fluid interconnect between the cannula and reservoir. That fluid connection must be extremely reliable and created with little energy. Thus, the insertion mechanism 600 must be extremely efficient and reliable.

FIGS. 11A-11D show insertion mechanism 600 in its second state: PBUP 517 has been removed and insertion mechanism 600 is ready to fire. The fluid path from reservoir 536 (FIG. 10G) is open to the atmosphere, and any residual pressure is vented before cannula insertion.

In simple terms, after removal of PBUP 517, when the patient pushes cannula trigger button 520, insertion mechanism 600 first causes trocar 647 and cannula 641 (best seen in FIG. 11D) to project out of disposable assembly 500 (that is state three, shown in FIGS. 12A and 12B), and then causes trocar 647 to retract back into insertion mechanism 600, leaving cannula 641 in place (which is state four, shown in FIGS. 13A-13D). Trocar 647, which includes an elongate rod with a sharp distal tip, may be made of metal, such as stainless steel, or other relatively rigid biocompatible material, such as rigid plastic, ceramic, or other rigid biocompatible material, and is used to penetrate the skin and a short distance into the flesh, to make a channel for cannula 641. Cannula 641 may be made of polytetrafluoroethylene (PTFE), such as TEFLON® PTFE, or other biocompatible polymeric material. The components involved and details of how insertion mechanism 600 performs these actions are described in more detail below.

Figure 11A:
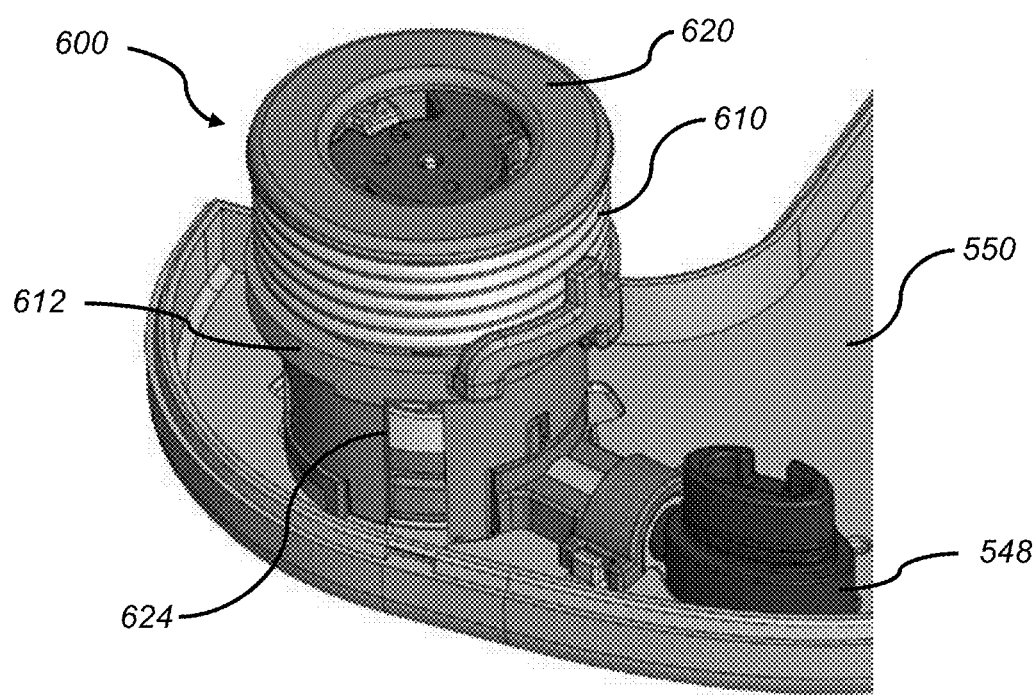
FIGS. 11A and 11B are perspective views of certain exemplary components of a disposable assembly, shown in state two, before cannula insertion.
Figure 11B:
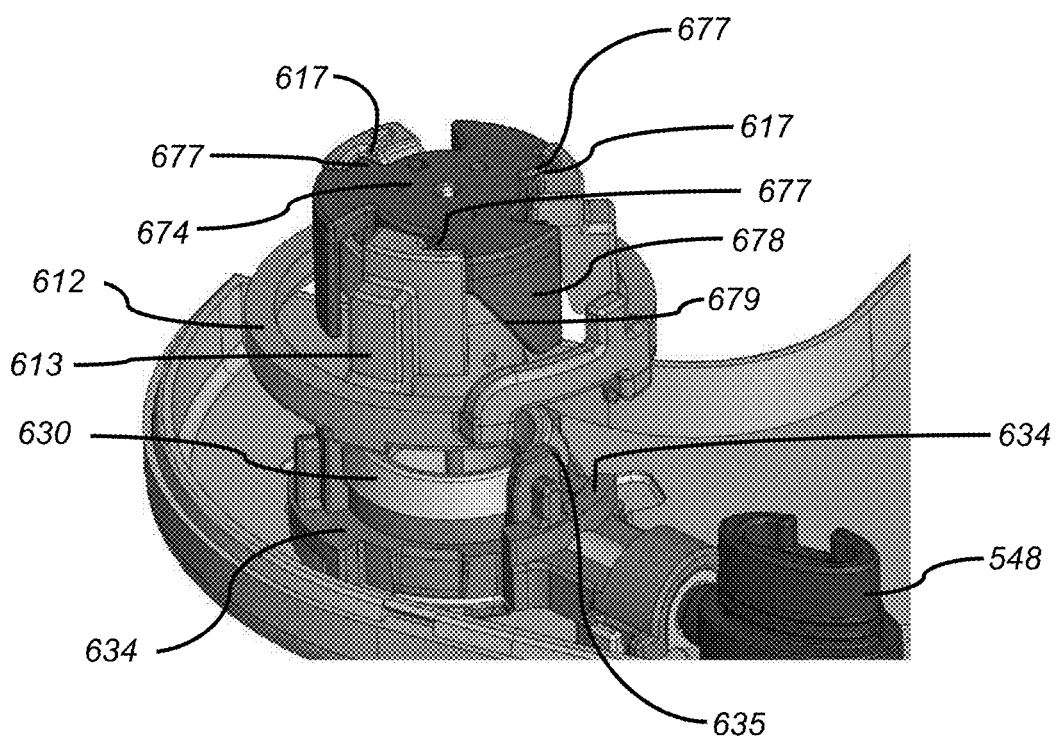
Figure 11C:
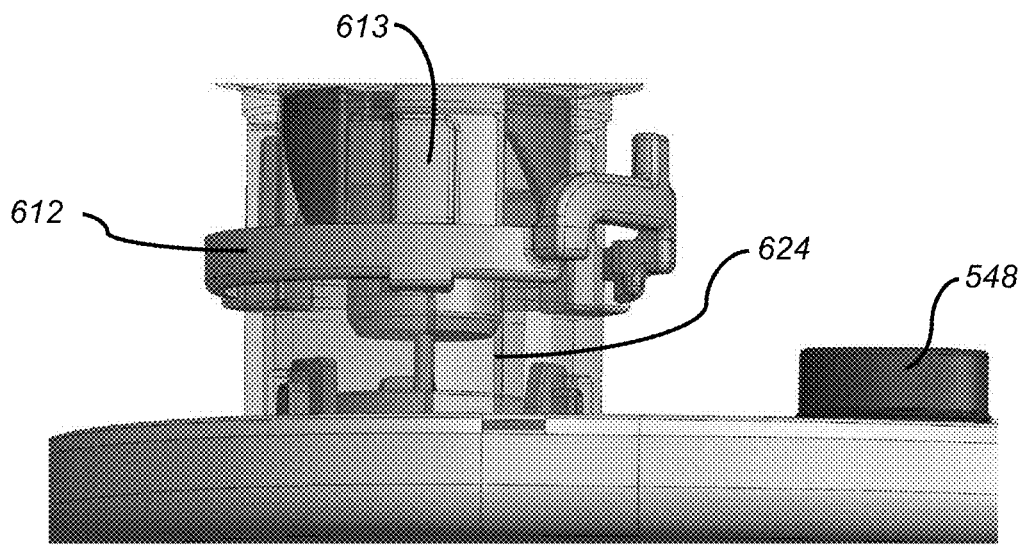
FIG. 11C is a side view showing additional exemplary components for use with the components of FIGS. 11A and 11B, shown in position before cannula insertion
Figure 11D:
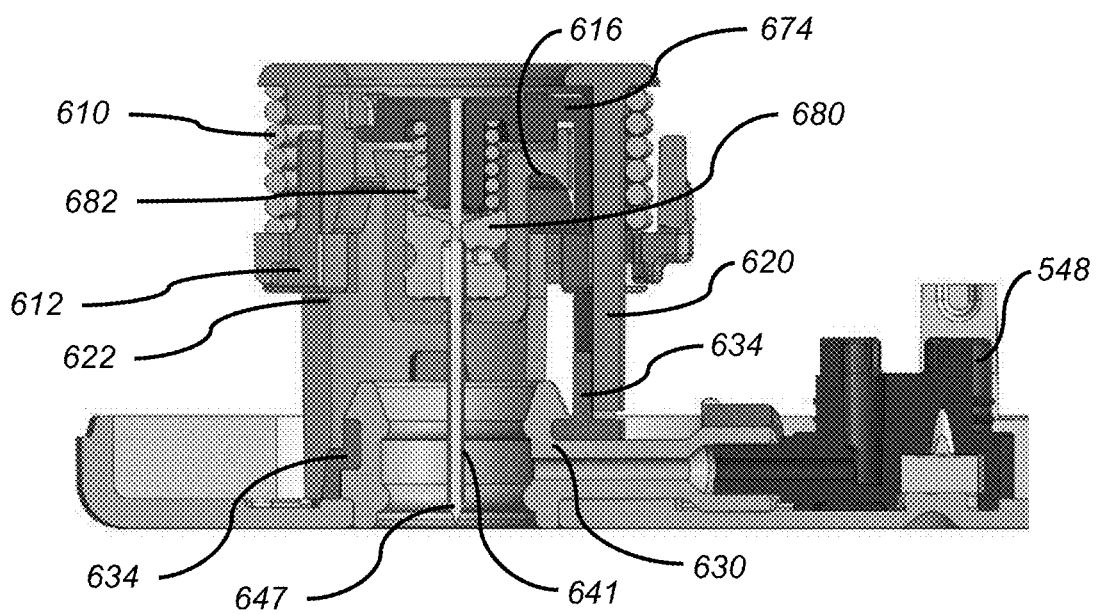
FIG. 11D is a section view showing additional exemplary components for use with the components of FIGS. 11A-11C, shown in position before cannula insertion.

As best seen in FIG. 11A, insertion mechanism 600 includes main insertion spring 610 and cannula carrier 612, which is supported on guide housing 620. Referring also to FIGS. 11B-11D, insertion mechanism 600 also includes trocar carrier 674, trocar seal 680, trocar retraction spring 682, cannula seal 630, and cannula seal retainer 634. As described further below, these components provide a highly efficient cannula seal with low cannula insertion forces and a highly reliable medicament seal.

FIG. 11B shows insertion mechanism 600 with main insertion spring 610 and guide housing 620 removed. In FIG. 11C, main insertion spring 610 is removed and guide housing 620 is semi-transparent. FIG. 11D is a section view of the components of FIG. 11C. Main insertion spring 610 may provide travel of about 7 mm with a starting force of about 15 newtons (N) and an ending force of about 7 N, and may be made of, for instance, 0.75 mm diameter music wire, with 6 turns and an outside dimension of 13.25 mm. Trocar retraction spring 682 may provide travel of about 7 mm with a starting force of about 4 N and an ending force of about 1 N, and may be made of, for instance, 0.5 mm diameter music wire, with 6 turns and an outside dimension of 3 mm. Guide housing 620 and cannula seal retainer 634 may be made of high strength plastic, such as nylon, acetal (Delrin®) or polycarbonate. Cannula carrier 612 and trocar carrier 674 may be made of COP, polypropylene or other similar drug-compatible material. Trocar seal 680 and cannula seal 630 may be made of elastomer, rubber, such as silicone rubber or bromobutyl rubber, or other relatively conformable sealing material that is also drug-compatible.

As mentioned above, FIGS. 11A-11D show insertion mechanism 600 in state two, the cocked position, before the patient pushes cannula trigger button 520 to cause cannula carrier 612 to drive cannula 641 into an inserted position. Before insertion, cannula carrier 612 is supported on support ledge 622 of guide housing 620 (best seen in FIG. 11D), which in turn holds main insertion spring 610 in a compressed state. Note that guide housing 620 does not move during cannula insertion.

When the user presses cannula trigger button 520, it pushes on trigger link 547, causing trigger link 547 to rotate. When trigger link 547 rotates, it pushes cannula carrier 612 counter-clockwise, causing cannula carrier 612 to slide off support ledge 622 of guide housing 620, and carrier tabs 613 to align with guide housing slots 624 (shown in FIGS. 11A and 11C). Once cannula carrier 612 is no longer supported by guide housing ledge 622, cannula carrier 612 can no longer resist the force of main insertion spring 610, and the elastic energy contained in main insertion spring 610 is converted to motion. Main insertion spring 610 then drives cannula carrier 612 with attached cannula 641, trocar carrier 674 with attached trocar 647, trocar seal 680, and trocar retraction spring 682 downward. As these components move downward, the sharp distal tip of trocar 647, which extends slightly beyond the distal end of cannula 641, penetrates the patient's skin, and cannula 641, which surrounds trocar 647, is inserted so the end of cannula 641 is about 6 mm below the surface of the patient's skin. At this point, insertion mechanism 600 in state three, as seen in FIGS. 12A and 12B.

Figure 12A:
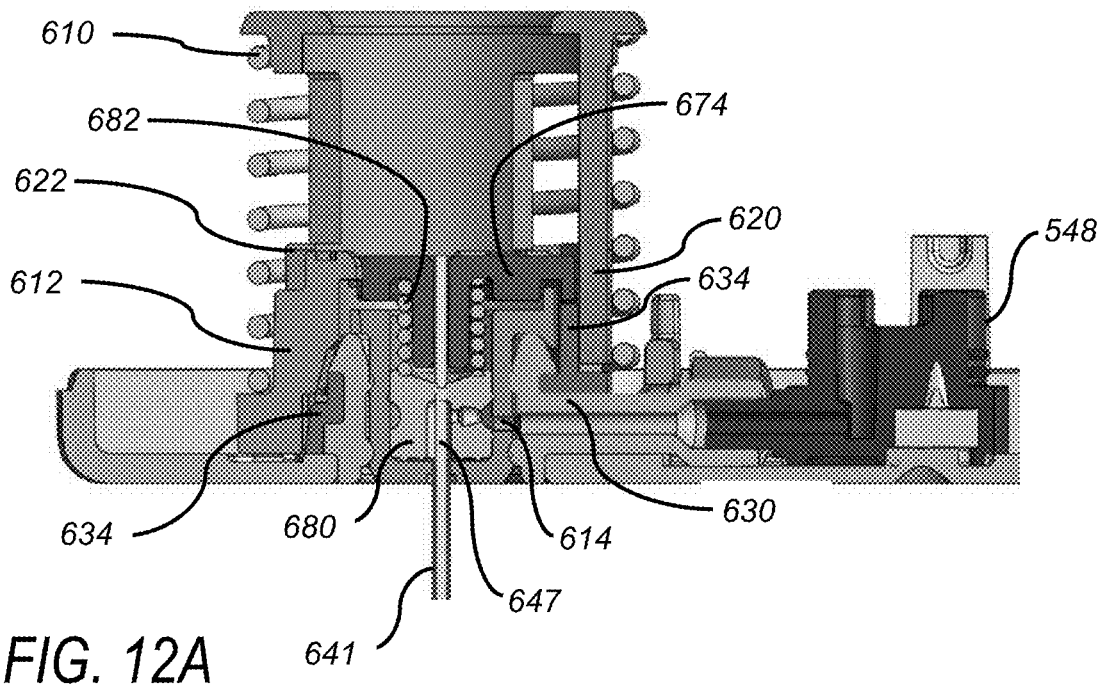
FIG. 12A is a section view of the components of FIG. 11D, shown in state three, after cannula insertion but before trocar retraction
Figure 12B:
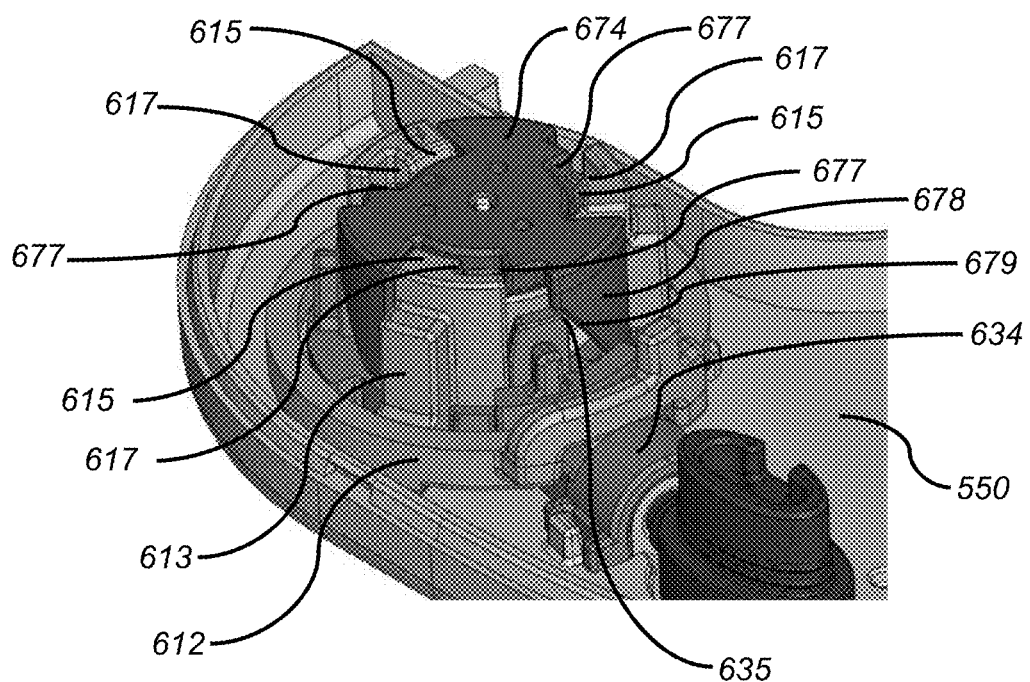
FIG. 12B is a perspective view showing additional exemplary components for use with the components of FIG. 12A, shown in position after cannula insertion but before trocar retraction.
Figure 13A:
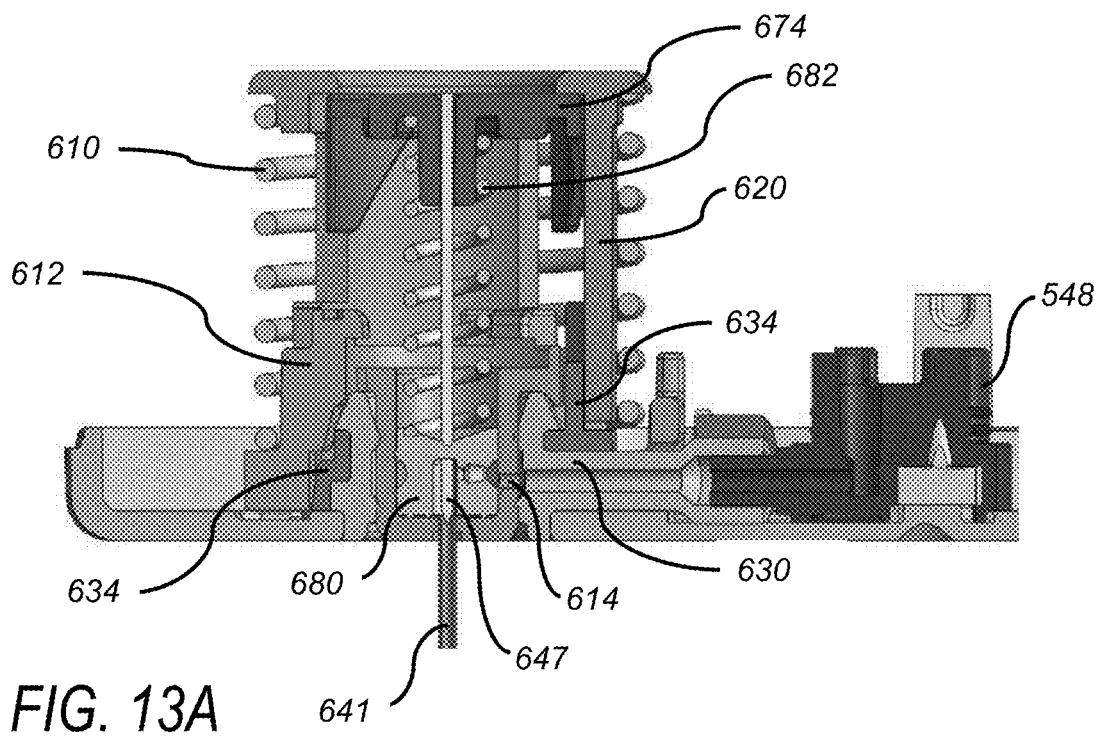
FIG. 13A is a section view of the components of FIGS. 11D and 12A, shown in state four, after cannula insertion and after trocar retraction.
Figure 13B:
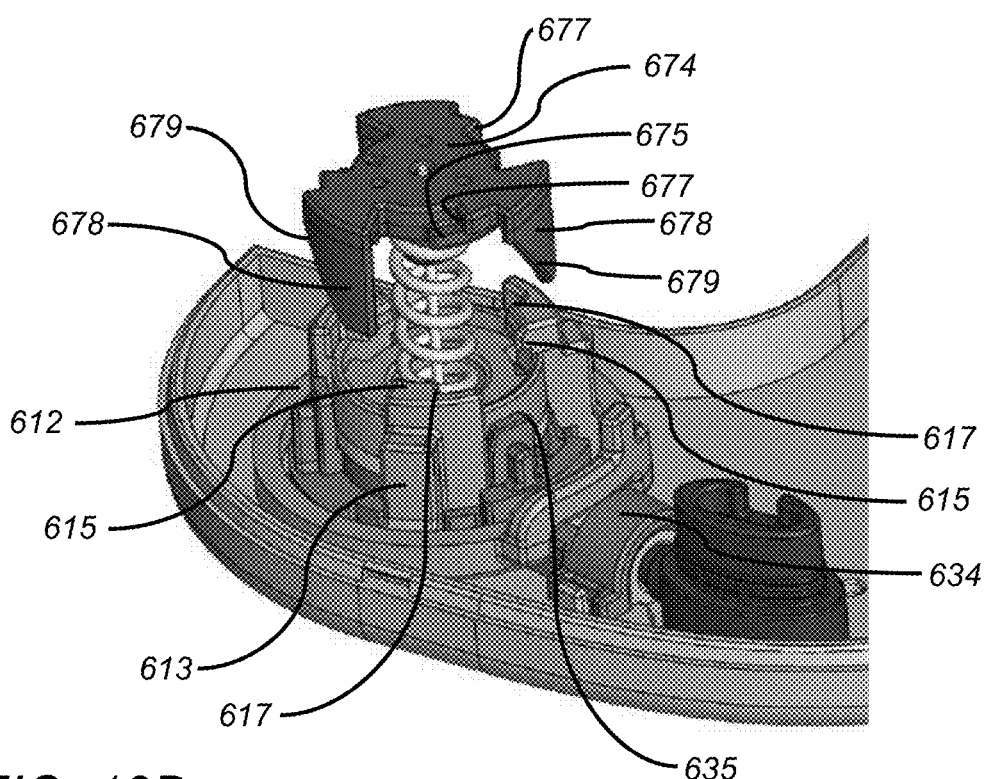
FIG. 13B is a perspective view showing additional exemplary components for use with the components of FIG. 13A, shown in position after cannula insertion and after trocar retraction.

As best seen in FIGS. 11B, 12B and 13B, cannula carrier 612 and trocar carrier 674 include features to lock them together before and during cannula insertion. Trocar carrier 674 includes locking ledges 675 that fit beneath locking bosses 615 on cannula carrier 612. When cannula carrier 612 and trocar carrier 674 are locked together, trocar retraction spring 682 is held in a compressed state. In addition, trocar carrier 674 includes locking ledge walls 677 that contact locking boss walls 617 on cannula carrier 612. These walls ensure that trocar carrier 674 moves only counter-clockwise together with cannula carrier 612, so trocar carrier's locking ledges 675 cannot accidently slide out from under cannula carrier's locking bosses 615 and unintentionally trigger penetration of trocar 647.

Once cannula carrier 612 and trocar carrier 674 are rotated to begin cannula insertion, and begin to move downward toward the patient, the angled edge 679 of trocar carrier tabs 678 contact corners 635 on seal retainer 634. As trocar carrier 674 moves downward, the contact between corners 635 and angled edges 679 causes trocar carrier 674 to rotate further and further counter-clockwise during cannula insertion. As cannula carrier 612 moves downward, carrier tabs 613 are positioned within guide housing slots 624 (shown in FIGS. 11A and 11C), allowing cannula carrier 612 to slide downward while preventing additional rotation of cannula carrier 612. As trocar carrier 674 rotates further counter-clockwise, trocar carrier's locking ledges 675 slide out from under cannula carrier's locking bosses 615.

FIGS. 12A and 12B show insertion mechanism 600 in state three: FIG. 12A shows main insertion spring 610 fully fired, cannula carrier 612 fully down, and cannula 641 fully inserted, at the instant trocar carrier 674 is released and before trocar retraction spring 682 drives trocar carrier 674 and trocar 647 upward. (As shown, the skin is pierced at about 90 degrees and the end of the cannula is positioned about 6 mm below the surface of the skin.) FIG. 12B shows the same instant, with main insertion spring 610 and guide housing 620 removed. This view shows the moment trocar carrier's locking ledges 675 are released from under cannula carrier's locking bosses 615.

Once trocar carrier's locking ledges 675 are released from under cannula carrier's locking bosses 615 (this is also the moment that cannula 641 is fully inserted, and insertion mechanism 600 in state three, as seen in FIGS. 12A and 12B), trocar carrier 674 can no longer resist the force of trocar retraction spring 682. The elastic energy contained in trocar retraction spring 682 is converted to motion, and trocar retraction spring 682 drives trocar carrier 674 with attached trocar 647 upward. As trocar carrier 674 moves upward, trocar 647 is removed from the patient and retracted back into insertion mechanism 600, leaving cannula 641 inserted. This is state four, as seen in FIGS. 13A-13D.

Figure 13C:
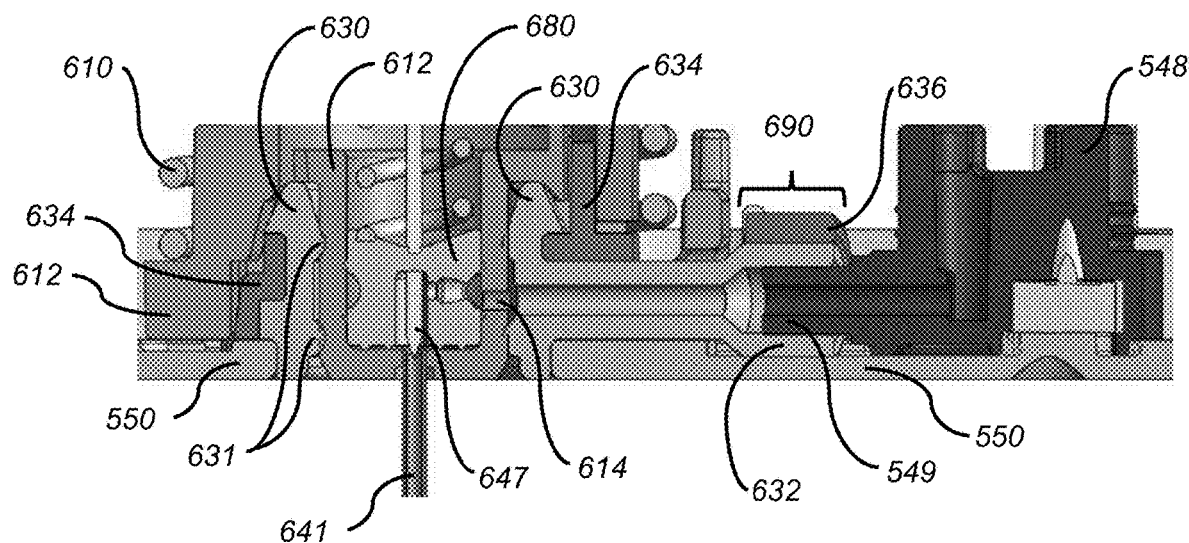
FIGS. 13C and 13D are section views of certain exemplary components of the assembly of FIG. 3A.

FIG. 13A is a section view showing insertion mechanism 600 fully fired and trocar 647 fully retracted. FIG. 13B shows more details of the fully fired insertion mechanism 600, with main insertion spring 610 and guide housing 620 removed. This is the position of the components of insertion mechanism 600 while exemplary ambulatory infusion system 100b is in use by the patient. The medicament path is best seen in FIGS. 13A and 13C. Broadly stated, medicament flows from the reservoir (not shown), to outlet fitting 548, into cannula seal 630, through channel 614 in cannula carrier 612, through trocar seal 680, and into cannula 641 for delivery to the patient.

Figure 13D:
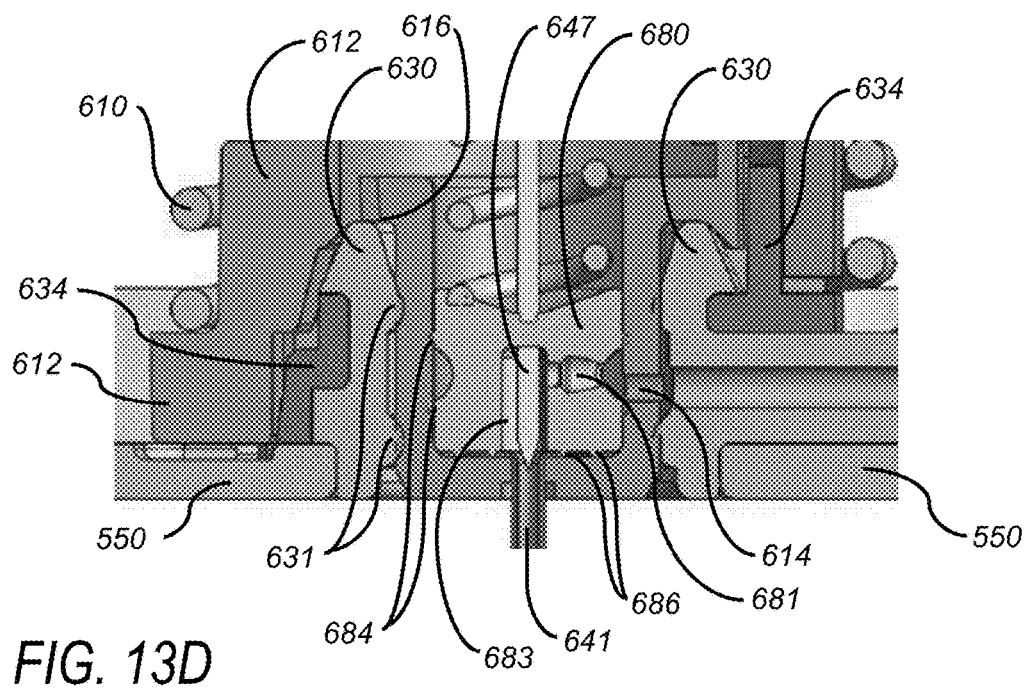

Best seen in FIGS. 13C and 13D is the highly efficient radial compression hydraulic seal formed between cannula carrier 612 and upper and lower seal rings 631 of cannula seal 630. Upper and lower seal rings 631 are separated by about 2.5 mm. Tapering of cannula seal 630 to the small contact areas of seal rings 631 concentrates surface stresses where the seal rings 631 contact cannula carrier 612, to provide a good seal. Additional upper and lower seal rings are possible, but could increase space requirements. To enhance the seal at seal rings 631, main insertion spring 610 exerts force on cannula carrier 612, holding it down against baseplate 550 and causing cannula carrier internal surface 616 to push on the top surface of cannula seal 630, as described in more detail below.

During the transition from state two to state three of insertion, cannula carrier internal surface 616 begins contacting the top of cannula seal 630 before the bottom surface of cannula carrier 612 contacts baseplate 550. When state three is reached, the bottom surface of cannula carrier 612 is held against baseplate 550 and cannula seal 630 is compressed from above. High-energy main insertion spring 610 improves sealing reliability, and cannula seal 630 acts as a bumper as it is compressed, helping dissipate the energy of insertion. Rather than being wasted, or converted to user-perceptible noise and feeling, residual energy from firing of main insertion spring 610 is converted from kinetic energy to enhanced radial compression of cannula seal 630.

In addition, the contact between cannula carrier internal surface 616 and the top surface of cannula seal 630 forms a secondary face seal. In state three, main insertion spring 610 continues pushing down on cannula carrier 612, with approximately 7-10 N of force. This force, spread over the top surface of cannula seal 630, results in a fluid seal capable of sealing approximately 3 bar, in addition to the seal maintained at the upper seal ring 631.

To further enhance this seal, seal retainer 634 provides radial support, acting as a fixed backing ring/clamp, increasing the radial compression around cannula seal 630. Even further enhancing the seal, cannula carrier 612 provides additional radial compression with clamping force on cannula seal 630, acting as an additional backing ring/clamp. The 7-10 N residual force derived from main insertion spring 610 results in downward (axial) compression on cannula seal 630, causing radial deformation of cannula seal 630, further improving the seal formed between cannula carrier 612 and seal rings 631. In state three, since cannula seal 630 is radially constrained by seal retainer 634 and cannula carrier 612, axial compression of cannula seal 630 causes radial deformation of seal 630, increasing the sealing force on sealing rings 631. All of this results in a highly efficient and reliable hydraulic cannula seal.

Turning now to FIG. 13C, the medicament path also includes a compression-type fitting 690 formed from clamp-portion 636 of seal retainer 634 clamping ferrule 632 of cannula seal 630 down onto barb 549 of outlet fitting 548. As an alternative, a separate component can be utilized to deliver the clamping forces provided by clamp-portion 636 of seal retainer 634. In addition, ferrule 632 of cannula seal 630 and barb 549 of outlet fitting 548 can be separate ferrule and barb components, but would introduce additional component interfaces along the medicament path, each requiring additional sealing features. In the configuration shown, cannula seal 630 seals cannula 641, absorbs energy during firing by compressing when struck by cannula carrier 612, and helps seal the reservoir with ferrule 632.

As best seen in FIG. 13D, medicament next flows through ferrule 632, through cannula seal 630, through channel 614 in cannula carrier 612, through trocar seal inlet 681, through trocar seal channel 683, and through cannula 641 for delivery to the patient. As can be seen from comparing FIGS. 11D, 12A, and 13A, trocar seal 680 remains in one position within cannula carrier 612 before, during, and after the insertion process, and remains in that position during patient use of exemplary ambulatory infusion system 100b. Trocar seal 680 includes sidewall seal rings 684 and base seal rings 686. Sidewall seal rings 684 prevent medicament leakage into cannula carrier 612 and, ultimately, into exemplary ambulatory infusion system 100b. Base seal rings 686 prevent leakage from around cannula 641, and ensure that medicament flowing from trocar seal inlet 681 and through trocar seal channel 683 is directed into cannula 641. FIG. 13D shows a pair of sidewall seal rings 684 and a pair of base seal rings 686, but additional seals may be used for additional leak protection.

Insertion mechanism 600 provides a highly efficient, highly reliable medicament seal with low insertion forces, all in a compact space. The energy supplied to insert cannula 641 is provided by main insertion spring 610, and needs to be sufficient to (a) allow trocar 647 to quickly and cleanly pierce the patient's skin for cannula insertion, (b) overcome friction forces during movement of cannula carrier 612 surfaces against cannula seal 630 surfaces and seal retainer 634 surfaces, and (c) result in compression and radial forces making a reliable medicament seal. Excess energy is absorbed by compression of cannula seal 630, which radially expands cannula seal 630, increasing the radial forces exerted by seal rings 631 against the surface of cannula carrier 612 and exerted by cannula seal 630 against seal retainer 634, as explained in more detail below. Energy requirements and expenditures are also described in more detail presently.

During operation, as insertion mechanism 600 transitions from state two to state three, the radial compression forces exerted on cannula seal 630 increase. As cannula carrier 612 begins moving downward, it first contacts upper cannula seal ring 631, and, generally, begins to capture and surround cannula seal 630 between the surfaces of cannula carrier 612 and seal retainer 634. Seal retainer 634 acts as a fixed backing ring, providing radial support for cannula seal 630, contributing to the radial clamping forces applied to cannula seal 630. However, in some alternatives, there may be a small gap between seal retainer 634 and cannula seal 630 until cannula seal 630 is compressed downward and expanded radially, as explained momentarily. The radial forces applied to cannula seal 630 increase as cannula carrier 612 continues moving downward, since the amount of contact, and therefore radial force, continues increasing between (i) the surfaces of cannula carrier 612 and cannula seal rings 631, (ii) seal retainer 634 and cannula seal 630, and (iii) in some alternatives, the surfaces of cannula carrier 612 and seal retainer 634. Contact between cannula carrier 612 and seal rings 631 during transition from state two to state three is also described in more detail below, in relation to the next embodiment.

As cannula carrier 612 continues moving downward, contact is made between the top surface of cannula seal 630 and carrier internal surface 616 (see FIGS. 11D and 13D). As explained above, this initial contact occurs while cannula carrier 612 is still moving downward. Therefore, as cannula carrier 612 continues moving downward, carrier internal surface 616 exerts increasing downward force on cannula seal 630, and as it does, cannula seal 630 is increasingly compressed as cannula carrier 612 continues moving. As carrier internal surface 616 pushes more and more on cannula seal 630 from above, cannula seal 630 expands more and more radially, resulting in additional radial compression forces between (i) seal rings 631 and cannula carrier 612 and (ii) cannula seal 630 and seal retainer 634. Cannula seal 630 may ultimately radially expand by, for instance, 0.5 mm. (In alternatives where there was a small gap between seal retainer 634 and cannula seal 630, this gap decreases until it is eliminated as cannula seal 630 expands radial due to downward compression of cannula seal 630 by carrier internal surface 616.) In addition, as described above, contact between cannula carrier internal surface 616 and the top surface of cannula seal 630 forms a secondary face seal. As such, a highly efficient and highly reliable cannula seal is achieved by (1) this face seal formed at cannula carrier internal surface 616 and the top surface of cannula seal 630, (2) contact between seal rings 631 and cannula carrier 612, (3) radial clamping forces exerted on cannula seal 630 by seal retainer 634, (4) increased radial clamping forces exerted by cannula carrier 612, acting as an additional backing ring (in addition to seal retainer 634) and providing increased radial compression of cannula seal 630, and (5) downward force exerted on the top of cannula seal 630 by cannula carrier 612 at cannula carrier internal surface 616, which expands cannula seal 630 radially and increases the radial forces exerted (a) by seal rings 631 against the surface of cannula carrier 612 and (b) by cannula seal 630 against seal retainer 634.

Another exemplary embodiment of an insertion mechanism 600a for a disposable assembly of an ambulatory infusion system is shown in FIGS. 14A-14F. This embodiment uses a moveable backing structure (part of cannula carrier 612a) that engages cannula seal 630a in state three, whereas the above embodiment uses a fixed backing ring (seal retainer 634) in addition to a moveable backing structure (part of cannula carrier 612). As described further below, this embodiment also provides a highly efficient radial compression seal with low cannula insertion forces and a highly reliable medicament seal.

As above, the energy supplied to insert cannula 641a is provided by a main insertion spring 610a (see FIGS. 14B and 14F), and needs to be sufficient to (a) allow trocar 647a to quickly and cleanly pierce the patient's skin for cannula insertion, (b) overcome friction forces during movement of cannula carrier 612a surfaces against cannula seal 630a surfaces, and (c) result in compression and radial forces making a reliable medicament seal. As above, excess energy is absorbed by compression of cannula seal 630a, which radially expands cannula seal 630a, increasing the radial forces exerted by seal rings 631a against cannula carrier 612a and exerted by cannula seal 630a against the angled surface of cannula carrier 612a, as explained in more detail below. As such and as above, rather than being wasted, or converted to user-perceptible noise and feeling, residual energy from firing of main insertion spring 610a is converted from kinetic energy to enhanced radial compression by cannula seal 630a.

Figure 14A:
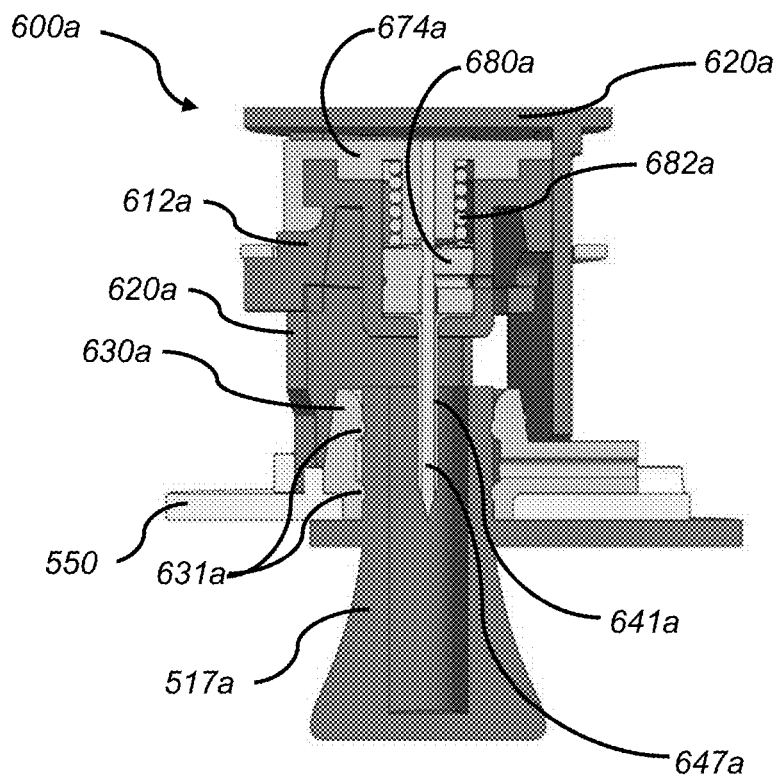
FIG. 14A is a section view showing certain alternative components of a disposable assembly, shown in state one, before pull-before-use plug, PBUP 517*a*, is removed.
Figure 14B:
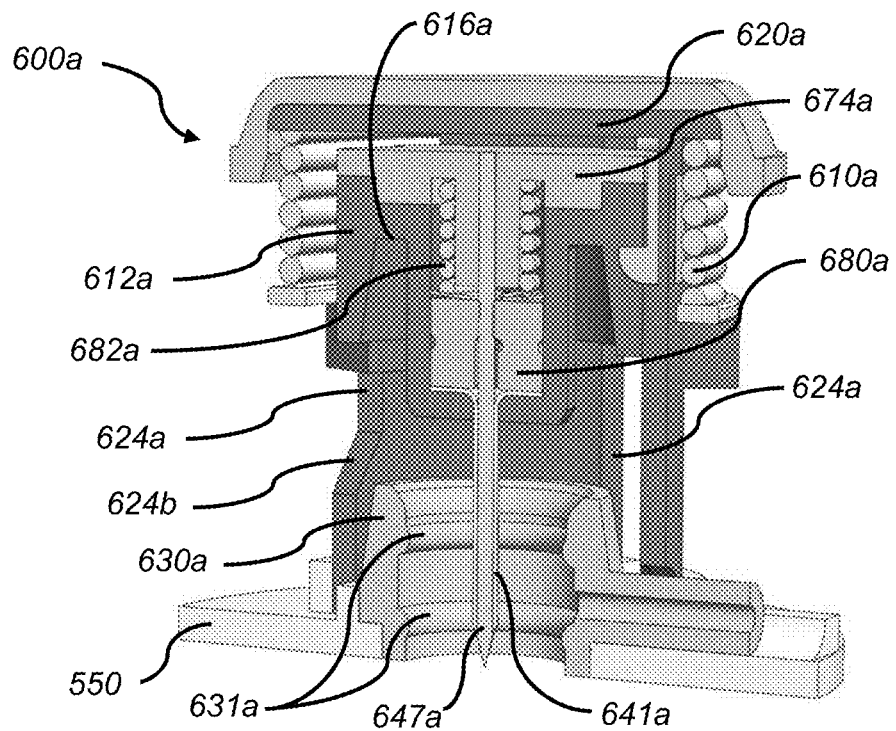
FIG. 14B is a perspective section view showing further alternative components of the disposable assembly of FIG. 14A, shown in state two, after PBUP 517*a* is removed but before cannula insertion.
Figure 14C:
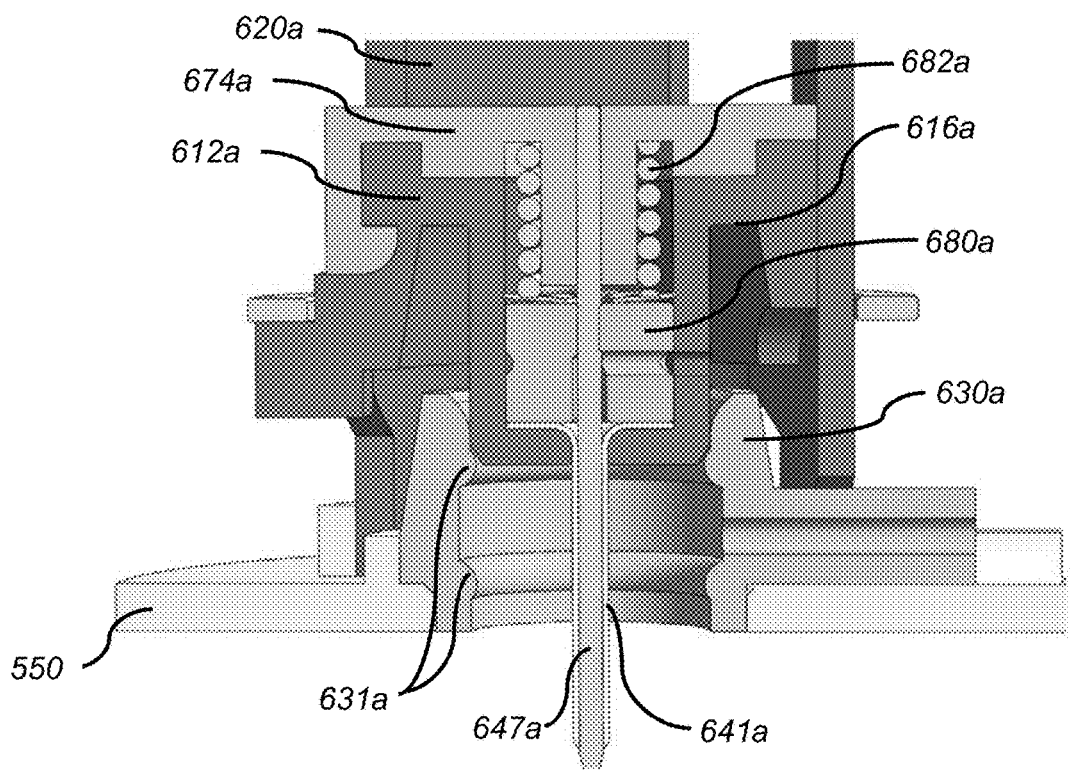
FIGS. 14C and 14D are section views of certain components and features of FIG. 14B, shown during transition from state two to state three, as the cannula is being inserted.
Figure 14D:
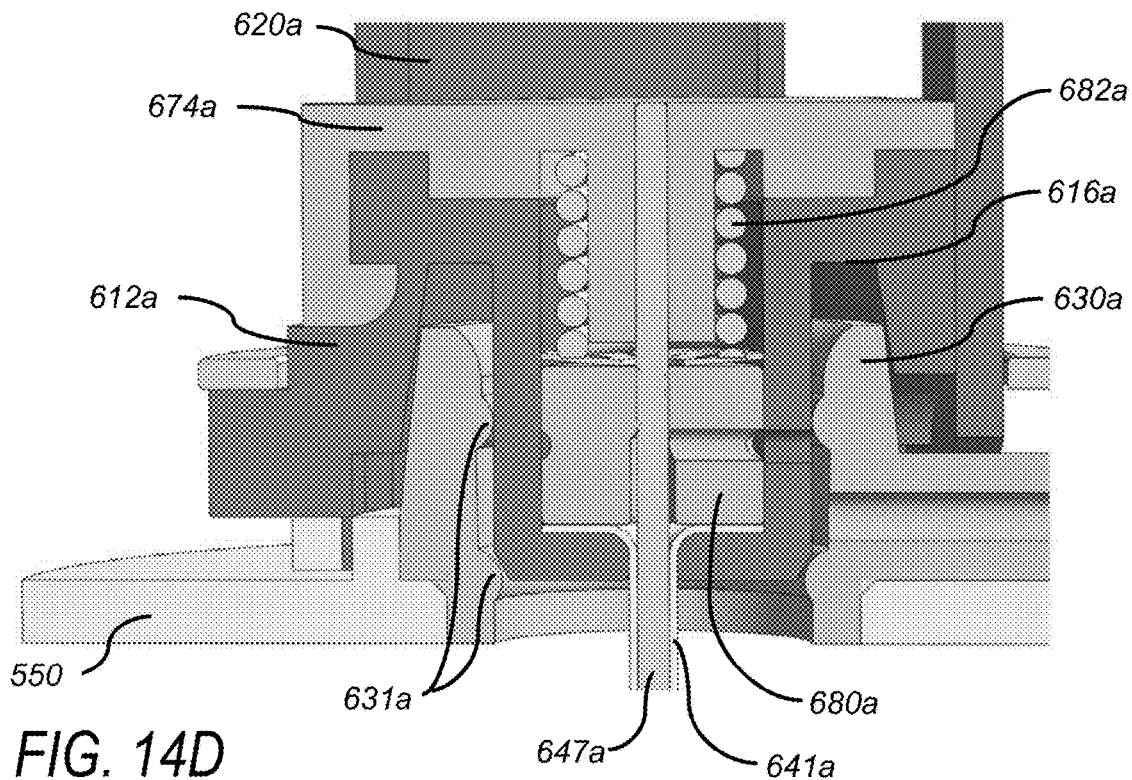
Figure 14E:
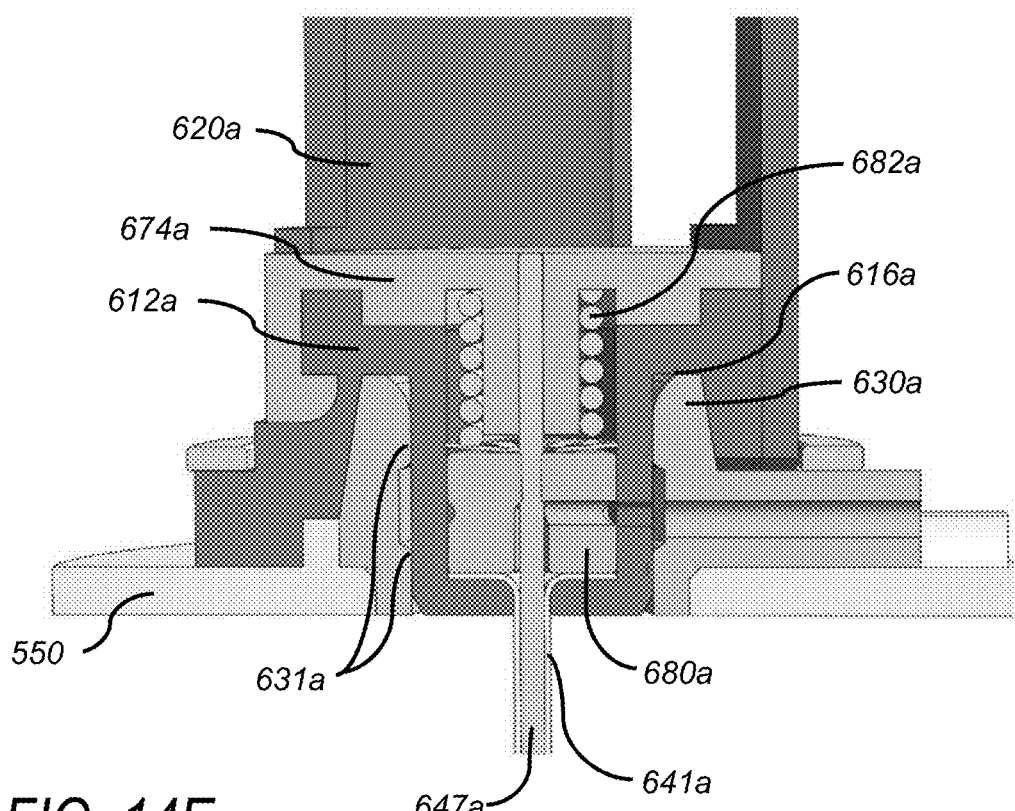
FIG. 14E is a section view of certain components and features of FIG. 14B, shown in state three, once the cannula is inserted.
Figure 14F:
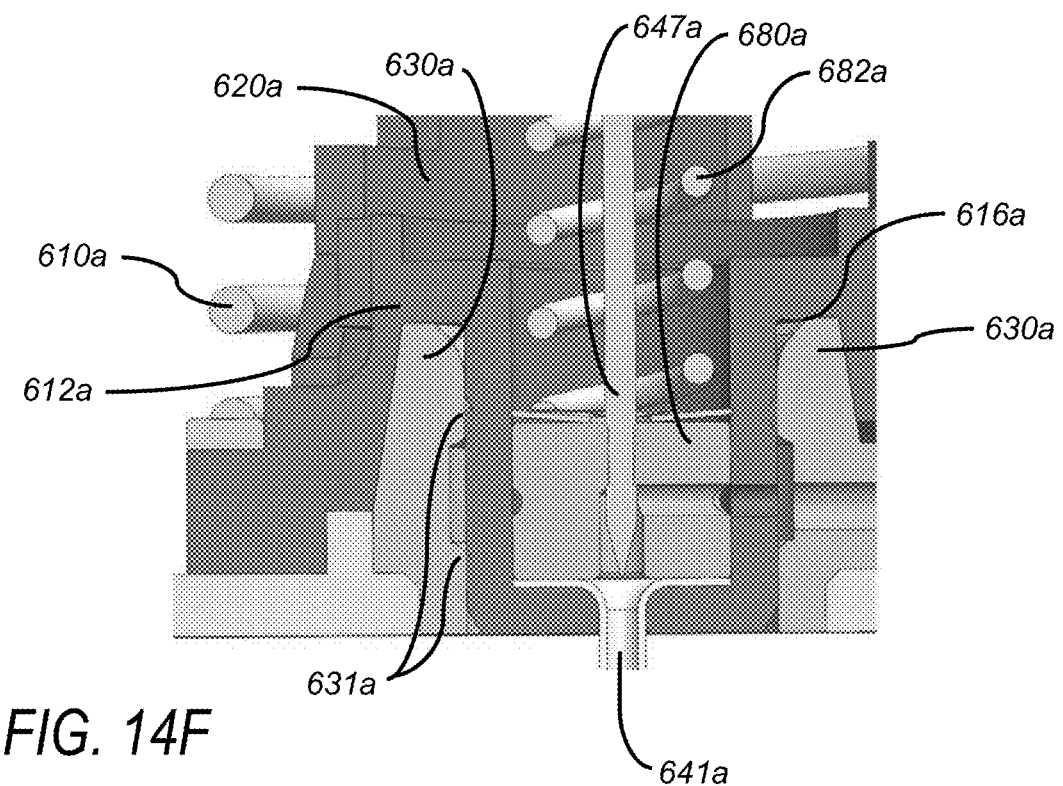
FIG. 14F is a section view of the certain components and features of FIG. 14B, shown in state four, after cannula insertion and after trocar retraction.

FIG. 14A is a section view certain components and features of insertion mechanism 600a shown in state one, before firing, and before pull-before-use plug, PBUP 517a, is removed. FIG. 14B is a section view of insertion mechanism 600a in state two, after PBUP 517a is removed but before firing of insertion mechanism 600a. FIGS. 14C and 14D are section views of certain components and features of FIG. 14B, shown during transition from state two to state three, as cannula 641a is being inserted. These views show details of cannula carrier 612a interaction with cannula seal 630a using a moveable backing structure. FIG. 14E is a section view of certain components and features of FIG. 14B, shown in state three, once cannula 641a is inserted but before trocar 647a is retracted. FIG. 14F is a closeup section view showing cannula carrier 612a, cannula seal 630a, and trocar seal 680a in state four, after firing of insertion mechanism 600a, cannula 641a insertion, and trocar 647a retraction. Some details of insertion mechanism 600a are omitted to simplify the views in FIGS. 14A-14F. For instance, insertion mechanism 600a may use a locking mechanism for cannula carrier 612a and trocar carrier 674a like that used by insertion mechanism 600, but those detailed features are not shown in FIGS. 14A-14F. Similarly, insertion mechanism 600a may use a cannula trigger button and trigger link like those used by insertion mechanism 600, and trocar seal 680a may include seal rings like those on trocar seal 680. Materials used for the components of insertion mechanism 600a may be similar to those described above for insertion mechanism 600.

FIGS. 14A and 14B show cannula carrier 612a supported on guide housing 620a, trocar 647a, trocar carrier 674a, trocar seal 680a, trocar retraction spring 682a, cannula seal 630a, seal rings 631a, and cannula 641a. FIG. 14A also shows PBUP 517a, and FIG. 14B also shows main insertion spring 610a. In this embodiment and as best seen in FIG. 14B, guide housing slots 624a include one or more tapers 624b that engage features on trocar carrier 674a, causing trocar carrier 674a to rotate further than cannula carrier 612a, so trocar carrier 674a disengages from cannula carrier 612a, allowing trocar retraction spring 682a to retract trocar into insertion mechanism 600a after cannula insertion.

In this embodiment, insertion mechanism 600a provides a cannula seal 630a that is radially unsupported before firing, because there is no cannula seal retainer. Instead, cannula carrier 612a provides all the radial compression forces in this embodiment. In other words, the previous embodiment uses a fixed backing ring (seal retainer 634), whereas this embodiment uses a moveable backing structure (part of cannula carrier 612a) that engages cannula seal 630a during transition from state two to state three, and remains engaged in state four. Insertion mechanism 600a still provides a highly efficient radial compression seal with low cannula insertion forces and a highly reliable medicament seal. That is, the radial compression forces exerted on seal 630a result in a reliable medicament seal following the insertion operation.

FIGS. 14C-14F show details of cannula carrier 612a interaction with cannula seal 630a in this embodiment that uses a moveable backing structure (part of cannula carrier 612a). FIG. 14C shows insertion mechanism 600a beginning to transition from state two to state three. As cannula carrier 612a begins traveling downwards, it first contacts upper seal ring 631a of cannula seal 630a and begins to capture and surround cannula seal 630a between the surfaces of cannula carrier 612a. FIG. 14D shows cannula carrier 612a after it has radially expanded upper seal ring 631a and is beginning to contact lower seal ring 631a. Upper and lower seal rings 631a are separated by about 2.5 mm. FIG. 14E shows insertion mechanism 600a in state three, with cannula 641a inserted but before trocar 647a retraction. In this state, and in state four, the initially expanded cannula seal 630a is in contact with the moveable backing structure of cannula carrier 612a, and has forced upper seal ring 631a into tight contact with cannula carrier 612a. The cannula carrier 612a has an angled inwardly facing surface (i.e., a surface that is not parallel or perpendicular to the downward movement direction, such as a frusto-conical surface) and the cannula seal 630a has an angled outwardly facing surface (i.e., a surface that is not parallel or perpendicular to the downward movement direction, such as a frusto-conical surface). The radial forces applied to cannula seal 630a increase as cannula carrier 612a moves downward, since the amount of contact, and therefore radial force, increases between (i) the vertical surface of cannula carrier 612a and cannula seal rings 631a and (ii) the angled surfaces of cannula carrier 612a and cannula seal 630a. A similar concept applies to the previous embodiment, where the amount of contact, and therefore radial force, increases, as cannula carrier 612 moves from state two to state four, between (i) the vertical surface of cannula carrier 612 and cannula seal rings 631 and (ii) cannula seal 630 and both seal retainer 634 and cannula carrier 612.

Also similar to the embodiment directly above, as cannula carrier 612 continues moving downward, contact is made between the top surface of cannula seal 630a and carrier internal surface 616a (see FIGS. 14A and 14B). This initial contact occurs while cannula carrier 612a is still moving downward. Therefore, as cannula carrier 612a continues moving downward, carrier internal surface 616a exerts increasing downward force on cannula seal 630a, and as it does, cannula seal 630a is increasingly compressed as cannula carrier 612a continues moving. As described above, this contact between cannula carrier internal surface 616a and the top surface of cannula seal 630a forms a secondary face seal. Also, as carrier internal surface 616a pushes more and more on cannula seal 630a from above, cannula seal 630a expands more and more radially, resulting in additional radial compression forces between (i) seal rings 631a and cannula carrier 612a and (ii) cannula seal 630a and the angled surface of cannula carrier 612a. Cannula seal 630a may ultimately radially expand by, for instance, 0.5 mm.

As such, a highly efficient and highly reliable cannula seal is achieved by (1) the face seal formed at cannula carrier internal surface 616a and the top surface of cannula seal 630a, (2) contact between seal rings 631a and cannula carrier 612a, (3) radial clamping forces exerted by cannula carrier 612a, acting as a moveable backing ring and providing radial compression of cannula seal 630a, and (4) downward force exerted on the top of cannula seal 630a by cannula carrier 612a at cannula carrier internal surface 616a, which expands cannula seal 630a radially and increases the radial forces exerted (a) by seal rings 631a against cannula carrier 612a and (b) by cannula seal 630a against the angled surface of cannula carrier 612a. This allows lower insertion forces for insertion of cannula carrier 612a, cannula 641a, trocar seal 680a, and trocar 647a into cannula seal 630a during firing, while the clamping action of cannula carrier 612a generates large radial forces on cannula seal 630a, maintaining a highly reliable hydraulic seal for leak-free operation. The minimized insertion forces may further allow minimizing of main insertion spring 610a size.

The energy required to transition the above insertion mechanisms between states will now be described. This explanation applies to insertion mechanism 600 and insertion mechanism 600a.

The energy required to transition from state one to state two is supplied by the user physically removing PBUP 517/517a. The energy required to transition insertion mechanism 600/600a from state two to state three is supplied by main insertion spring 610/610a. This energy is composed mainly of skin piercing energy and seal insertion energy, and secondarily of mechanism friction, compression of cannula seal 630/630a, and triggering of trocar retraction. The energy to transition from state three to state four is supplied by trocar retraction spring 682/682a. This discussion focuses on the transition from state two to state three, when the cannula is inserted and sealing of the medicament path is accomplished.

Skin piercing energy was modeled, based on the forces required to pierce the skin and move the cannula to the correct insertion depth. As mentioned earlier, the tip (distal end) of cannula 641/641a is inserted to a depth of about 6 mm. Skin piercing force begins at 0 N, rises to a maximum of approximately 5 N when the tip is about 2 mm subcutaneous, then drops to approximately 3 N when the tip reaches its final 6 mm position. This results in approximately 21 N-mm energy for skin piercing.

Seal insertion energy should be minimized. In the two embodiments directly above, the sealing surface of cannula carrier 612/612a has a diameter of about 5 mm, and requires cannula seals spaced approximately 2.5 mm apart. This means upper seal ring 631/631a engages cannula carrier 612/612a when cannula carrier 612/612a still has about 3.5 mm to travel before cannula 641/641a reaches state three (about 6 mm below the surface of the patient's skin) and lower seal ring 631/631a engages cannula carrier 612/612a about 1.0 mm before cannula 641/641a reaches state three.

Effective seal design requires the seal contact stress to be at least the pressure of the fluid to be sealed. As an example, if maximum medicament fluid pressure is 3 bar (gauge), and seal rings 631/631a have a contact width of about 1 mm each (and diameter of about 5 mm, as stated above), this results in a seal radial force of about 4.8 N minimum each for the upper and lower seals. Factoring in design margins/tolerances and an assumed coefficient of friction of 0.8 for elastomers on plastics, this results in a calculated design insertion force of approximately 5 N for each seal ring 631/631*a*. From an energy view, this represents about 17.5 N-mm (3.5 mm×5 N) for upper seal ring 631/631*a* and 5 N-mm (1 mm×5 N) for lower seal ring 631/631*a* for the transition between state two and state three.

The mechanisms of insertion mechanism 600/600*a* are linear, with low friction losses. In the example given earlier, the main insertion spring provides 77 N-mm total energy. Given about 21 N-mm for skin piercing energy, about 17.5 N-mm for upper seal ring seal insertion energy, and about 5 N-mm for lower seal ring insertion energy, totaling about 43.5 N-mm, this leaves about 33.5 N-mm for friction, compression of cannula seal 630/630*a*, and for triggering the trocar retraction mechanism. This amount of reserve energy may not be necessary, so less spring force may be sufficient. The insertion mechanisms proposed herein are energy-efficient, as well as highly reliable, compact, inexpensive, and user-friendly.

Various methodologies and systems are presented here in the context of the exemplary structures described in the preceding sections, and illustrated in the various figures, for the purpose of explanation only. Although the present methodologies and systems may employ the structures described above, they are not limited thereto. Additionally, embodiments of the present inventions may incorporate any one, combinations of less than all, or all of the methodologies or devices referenced above.

Although the inventions disclosed herein have been described in terms of the preferred embodiments above, numerous modifications and/or additions to the above-described preferred embodiments would be readily apparent to one skilled in the art. By way of example, but not limitation, the present inserter and sealing assemblies may be incorporated into fully disposable infusion pumps. It is intended that the scope of the present inventions extends to all such modifications and/or additions and that the scope of the present inventions is limited solely by the claims set forth below or later added.

Finally, with respect to terminology that may be used herein, whether in the description or the claims, the following should be noted. The terms "comprising," "including," "carrying," "having," "containing," "involving," and the like are open-ended and mean "including but not limited to." Ordinal terms such as "first", "second", "third," do not, in and of themselves, connote any priority, precedence, or order of one element over another or temporal order in which steps of a method are performed. Instead, such terms are merely labels to distinguish one element having a certain name from another element having a same name (but for the ordinal term) to distinguish the elements. "And/or" means that the listed items are alternatives, but the alternatives also include any combination of the listed items. The terms "approximately," "about," "substantially" and "generally" allow for a certain amount of variation from any exact dimensions, measurements, and arrangements, and should be understood within the context of the description and operation of the invention as disclosed herein. Terms such as "top," "bottom," "upper," "lower," "above," and "below" are terms of convenience that denote the spatial relationships of parts relative to each other rather than to any specific spatial or gravitational orientation. Thus, the terms are intended to encompass an assembly of component parts regardless of whether the assembly is oriented in the particular orientation shown in the drawings and described in the specification, upside down from that orientation, or any other rotational variation therefrom.

What is claimed is:

1. A cannula insertion mechanism, comprising:
    a seal configured to surround an opening of a housing, the seal including a first seal surface and a second seal surface, the first seal surface facing toward the opening, and the second seal surface facing away from the opening; and
    a cannula;
    a cannula carrier surrounding at least a portion of the cannula and configured to drive the cannula in a first direction through the opening of the housing, the cannula carrier having a first carrier surface and a second carrier surface, the first carrier surface being configured to exert a compression force on the second seal surface when the cannula carrier drives the cannula in the first direction, thereby causing the first seal surface to expand in a second direction to engage the second carrier surface such that, when the cannula carrier is seated within the housing with the cannula in an inserted position, the cannula carrier radially compresses the seal.

2. The cannula insertion mechanism of claim 1, wherein the first seal surface comprises one or more seal rings.

3. The cannula insertion mechanism of claim 1, wherein the first seal surface is substantially perpendicular to the second seal surface, and wherein the first direction is substantially perpendicular to the second direction.

4. The cannula insertion mechanism of claim 1, further comprising a seal retainer configured to exert a clamping force on the seal at a third seal surface that is opposite the first seal surface.

5. The cannula insertion mechanism of claim 1, wherein the cannula carrier includes a third carrier surface configured to exert a clamping force on the seal at a third seal surface.

6. The cannula insertion mechanism of claim 5, wherein the third carrier surface and the third seal surface are angled surfaces configured to engage each other.

7. The cannula insertion mechanism of claim 1, further comprising a trocar carrier configured to be coupled to the cannula carrier until the cannula is driven through the opening of the housing.

8. The cannula insertion mechanism of claim 7, further comprising:
    a trocar retraction spring that is held in a compressed state between the trocar carrier and the cannula carrier when the trocar carrier is coupled to the cannula carrier.

9. The cannula insertion mechanism of claim 8, wherein the trocar carrier is configured to decouple from the cannula carrier based on rotation relative to the cannula carrier, the rotation allowing the trocar retraction spring to drive the trocar carrier in a third direction opposite the first direction.

10. The cannula insertion mechanism of claim 9, wherein the rotation is caused by an angled surface of the trocar carrier engaging a fixed surface as the cannula is driven in the first direction.

11. A fluid delivery device comprising:
    a housing;
    a cannula; and
    a cannula insertion mechanism comprising:
        a seal configured to surround an opening of the housing, the seal including a first seal surface and a second seal surface, the first seal surface facing toward the opening, and the second seal surface facing away from the opening; and
        a cannula carrier surrounding at least a portion of the cannula and configured to drive the cannula in a first direction through the opening of the housing, the cannula carrier having a first carrier surface and a second carrier surface, the first carrier surface being configured to exert a compression force on the second seal surface when the cannula carrier drives the cannula in the first direction, thereby causing the first seal surface to expand in a second direction to engage the second carrier surface, such that, when the cannula carrier is seated within the housing with the cannula in an inserted position, the cannula carrier radially compresses the seal.

12. The fluid delivery device of claim 11, wherein the first seal surface comprises one or more seal rings.

13. The fluid delivery device of claim 11, wherein the first seal surface is substantially perpendicular to the second seal surface, and wherein the first direction is substantially perpendicular to the second direction.

14. The fluid delivery device of claim 11, further comprising a seal retainer configured to exert a clamping force on the seal at a third seal surface that is opposite the first seal surface.

15. The fluid delivery device of claim 11, wherein the cannula carrier includes a third carrier surface configured to exert a clamping force on the seal at a third seal surface.

16. The fluid delivery device of claim 15, wherein the third carrier surface and the third seal surface are angled surfaces configured to engage each other.

17. The fluid delivery device of claim 11, further comprising a trocar carrier configured to be coupled to the cannula carrier until the cannula is driven through the opening of the housing.

18. The fluid delivery device of claim 17, further comprising:
   a trocar retraction spring that is held in a compressed state between the trocar carrier and the cannula carrier when the trocar carrier is coupled to the cannula carrier.

19. The fluid delivery device of claim 18, wherein the trocar carrier is configured to decouple from the cannula carrier based on rotation relative to the cannula carrier, the rotation allowing the trocar retraction spring to drive the trocar carrier in a third direction opposite the first direction.

20. The fluid delivery device of claim 19, wherein the rotation is caused by an angled surface of the trocar carrier engaging a fixed surface as the cannula is driven in the first direction.

* * * * *